(12) United States Patent
Bradbury et al.

(10) Patent No.: US 7,135,310 B2
(45) Date of Patent: Nov. 14, 2006

(54) METHOD TO AMPLIFY VARIABLE SEQUENCES WITHOUT IMPOSING PRIMER SEQUENCES

(75) Inventors: Andrew M. Bradbury, Sante Fe, NM (US); Ahmet Zeytun, Los Alamos, NM (US)

(73) Assignee: The Regents of the University of California, Oakland, CA (US)

( * ) Notice: Subject to any disclaimer, the term of this patent is extended or adjusted under 35 U.S.C. 154(b) by 671 days.

(21) Appl. No.: 10/167,634

(22) Filed: Jun. 11, 2002

(65) Prior Publication Data

US 2003/0207282 A1 Nov. 6, 2003

Related U.S. Application Data

(63) Continuation-in-part of application No. 10/132,067, filed on Apr. 24, 2002, now abandoned.

(51) Int. Cl.
*C12P 19/34* (2006.01)
(52) U.S. Cl. ..................... 435/91.1; 435/91.2
(58) Field of Classification Search ............... 435/6, 435/91.1, 91.2; 536/23.1, 24.33
See application file for complete search history.

(56) References Cited

U.S. PATENT DOCUMENTS

| | | | | |
|---|---|---|---|---|
| 5,739,310 A | * | 4/1998 | Yao et al. .................. | 536/24.5 |
| 6,025,485 A | * | 2/2000 | Kamb et al. ............. | 536/25.32 |
| 6,063,604 A | * | 5/2000 | Wick et al. ................ | 435/91.2 |
| 6,190,889 B1 | * | 2/2001 | Jones ......................... | 435/91.1 |
| 6,291,158 B1 | | 9/2001 | Winter et al. | |
| 6,291,159 B1 | | 9/2001 | Winter et al. | |
| 6,291,160 B1 | | 9/2001 | Lerner et al. | |
| 6,291,161 B1 | | 9/2001 | Lerner et al. | |
| 6,329,201 B1 | * | 12/2001 | Polo et al. ............... | 435/320.1 |
| 6,358,733 B1 | * | 3/2002 | Motwani et al. ......... | 435/320.1 |
| 6,475,736 B1 | | 11/2002 | Stanton, Jr. | |
| 2002/0065609 A1 | * | 5/2002 | Ashby ........................ | 702/20 |
| 2002/0081598 A1 | | 6/2002 | Evens et al. | |
| 2003/0073101 A1 | | 4/2003 | Olson et al. | |

FOREIGN PATENT DOCUMENTS

| | | | |
|---|---|---|---|
| EP | 0 368 684 B1 | | 11/1989 |
| EP | 0 587 312 A2 | | 8/1993 |
| WO | 0368684 | * | 3/1994 |
| WO | WO 01/30851 A2 | | 5/2001 |
| WO | WO 01/30851 A3 | | 5/2001 |
| WO | WO 01/75091 A2 | | 10/2001 |
| WO | WO 01/79481 A2 | | 10/2001 |
| WO | WO 01/79481 A3 | | 10/2001 |

OTHER PUBLICATIONS

Szybalski et al. Class-IIs restriction enzymes—a review. Gene, vol. 100, pp. 13-26, Apr. 1991.*
Pingoud et al. Structure and function of type II restriction endonucleases. Nucleic acids Research, vol. 29, No. 18, pp. 370 3727, 2001.*

* cited by examiner

Primary Examiner—Kenneth R. Horlick
Assistant Examiner—Cynthia Wilder
(74) Attorney, Agent, or Firm—Townsend and Townsend and Crew LLP

(57) ABSTRACT

The present invention provides methods of amplifying target sequences without including regions flanking the target sequence in the amplified product or imposing amplification primer sequences on the amplified product. Also provided are methods of preparing a library from such amplified target sequences.

43 Claims, 1 Drawing Sheet

METHOD TO AMPLIFY VARIABLE SEQUENCES WITHOUT IMPOSING PRIMER SEQUENCES

CROSS-REFERENCES TO RELATED APPLICATIONS

This application is a continuation in part of U.S. patent application Ser. No. 10/132,067 filed Apr. 24, 2002 now abandoned, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under grant number DE-FG02-98ER62647 from the United States Department of Energy and Contract No. W-7405-ENG-36 awarded by the United States Department of Energy to The Regents of The University of California. The government has certain rights in this invention.

REFERENCE TO A "SEQUENCE LISTING," A TABLE, OR A COMPUTER PROGRAM LISTING APPENDIX SUBMITTED ON A COMPACT DISK.

Not applicable.

BACKGROUND OF THE INVENTION

Methods for amplifying nucleic acids provide useful tools for the detection of human pathogens, detection of human genetic polymorphisms, detection of RNA and DNA sequences, for molecular cloning, sequencing of nucleic acids, and the like. In particular, the polymerase chain reaction (PCR) has become an important tool in the cloning of DNA sequences, forensics, paternity testing, pathogen identification, disease diagnosis, and other useful methods where the amplification of a nucleic acid sequence is desired. (See e.g., PCR Technology: Principles and Applications for DNA Amplification (See, Erlich, ed., 1992); PCR Protocols: A Guide to Methods and Applications (See, Innis et al., eds, 1990)).

PCR permits the copying, and resultant amplification, of a target nucleic acid. Briefly, a target nucleic acid, e.g. DNA, is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

In general, PCR and other methods of amplification use primers which anneal to either end of the DNA of interest. While such methods are easy when there is only a single target, and the ends are well defined and invariable, they become more difficult when there are multiple targets in which the sequences are not identical. This is a particular problem with antibody variable genes and the hypervariable regions within variable genes, especially in the creation of ligand libraries where unbiased amplification and cloning of numerous different ligands is required. Degenerate primers which anneal to regions of similarity (but not identity) at the ends of the variable gene and primers which anneal to constant sequences flanking the antibody variable gene have been used to overcome this problem. Each of these approaches, however, has disadvantages. For example, using degenerate primers may introduce foreign sequences into the priming site and also may not amplify all members of the library. Furthermore, amino acid modification as a result of these changes have adversely affected solubility, expression levels, and affinity. (See, e.g. de Haard H J, et al. (1998) *Protein Eng.* 11(12):1267. Honegger and Pluckthun (2001) *J Mol Biol.* 309(3):687.). Using primers which anneal to constant sequences flanking the antibody variable gene also typically may lead to the addition of extra conserved sequences to the variable sequences of interest, which may not be required.

The complementarity determining regions (CDRs) of immunoglobulin molecules have evolved over millions of years to specifically bind antigens within the context of the immunoglobulin molecule structure. The immunoglobulin molecule structure provides a scaffold for the CDRs so that they can extend out and contact antigen. During the maturation of antibody producing B cells, recombinations of variable region encoding genes, V, D, and J. Recombinations of V, D, and J which do not create functional antibody genes have their expression levels downregulated. As a result, most of the mRNA which can be isolated from circulating lymphocytes corresponds to functional V genes. The CDRs found within such functional V genes, and hence mRNA, thus provide a very rich source of potential binding elements. Although such CDRs could be amplified using primers annealing to the adjacent antibody framework regions, the PCR products arising from such an amplification, would always have the framework regions recognized by such primers attached to the PCR product. In applications in which CDRs would be transplanted from antibodies to another scaffold, such framework regions may interfere with the correct folding of the scaffold. Because of the high degree of variablility of the antibody hypervariable regions, there has been no method available to isolate variable or hypervariable regions, free of flanking sequences.

Thus, there is a need in the art for a method of amplifying target sequences without including regions flanking the target sequence in the amplified product or imposing primer sequences on the amplified product.

BRIEF SUMMARY OF THE INVENTION

The present invention provides a method of amplifying target sequences without including regions flanking the target sequence in the amplified product or imposing primer sequences on the amplified product.

One embodiment of the present invention provides a method of preparing an amplified product that is free of amplification primer sequences. The target nucleic acid sequence is amplified in an amplification reaction comprising: (1) a first primer that specifically anneals to a region upstream of a target polynucleotide sequence, wherein the first primer comprises a first restriction enzyme recognition site that is recognized by a restriction enzyme that cleaves at a distance from the recognition site; and (2) a second primer that specifically anneals to a region downstream of the target polynucleotide sequence, wherein the second primer comprises a second restriction enzyme recognition site that is recognized by a restriction enzyme that cleaves at a distance from the recognition site. The amplified product is cleaved with the first and second restriction enzymes, thereby obtaining the amplified target that is free of amplification primer sequences. At least one restriction enzyme may cleave at two sites at a distance from its recognition site. At least one restriction enzyme recognition site may be a non-palindromic sequence, a palindromic sequence, an interrupted sequence, or a contiguous sequence. At least one restriction enzyme may cleave at a position at least 6 base pairs downstream of its recognition site. The first and second restriction enzyme recognition sites may be the same. At least one of the restriction enzymes may be BpmI, EcoP15I, Bce83I, BsgI, Eco57I, GsuI, MmeI, AloI, BaeI, BcgI, BplI, BsaXI, Bsp24I, CjeI, FalI, PpiI, or PsrI. The target polynucleotide sequence may be an antibody variable region, an antibody hypervariable (CDR) region, a T cell receptor variable or hypervariable region, or any family of genes which comprise variable parts and relatively constant parts. The first and second primers may specifically hybridize to the region encoding an antibody framework region, or to the regions flanking an antibody variable region (i.e., leader sequence and constant regions).

Another embodiment of the invention provides a method of preparing a library. An amplified product that is free of amplification primer sequences is prepared by amplifying the target nucleic acid sequence in an amplification reaction. The amplification reaction comprises (1) a first primer that specifically anneals to a region upstream of a target polynucleotide sequence, wherein the first primer comprises a first restriction enzyme recognition site that is recognized by a restriction enzyme that cleaves at a distance from the recognition site; and (2) a second primer that specifically anneals to a region downstream of the target polynucleotide sequence, wherein the second primer comprises a second restriction enzyme recognition site that is recognized by a restriction enzyme that cleaves at a distance from the recognition site. The amplified product is cleaved with the first and second restriction enzymes, thereby obtaining the amplified target that is free of amplification primer sequences. The amplified product may be linked to a library vehicle. A library vehicle may comprise a cloning vector such as a phage display vector, a bacterial vector, or a yeast vector. The library vehicle may comprise a nucleic acid encoding an enzyme, a heterologous protein, a GFP scaffold, or a coat protein. The library vehicle may comprise an oligonucleotide joined to puromycin. The library vehicle may comprise a ribosome. The step of linking the amplified product to a library vehicle may comprise ligating an adaptor oligonucleotide to the amplified product, thereby forming a linked amplified product; and amplifying the linked ligated product. The linked amplified product may be further linked to an oligonucleotide. Oligonucleotides linked to the 5' and 3' ends of the amplified product may be the same or different. The oligonucleotide may be a sequence that hybridizes to a sequence encoding a restriction enzyme recognition site. The oligonucleotide may be a sequence that hybridizes to a sequence encoding a protein. The protein may be a heterologous or a homologous protein. The oligonucleotide may be a sequence that hybridizes to a sequence encoding a recombination site.

At least one restriction enzyme may cleave at two sites at a distance from its recognition site. At least one restriction enzyme recognition site may be a non-palindromic sequence, a palindromic sequence, an interrupted sequence, or a contiguous sequence. At least one restriction enzyme may cleave at a position at least 6 base pairs or at least 9 base pairs downstream of its recognition site. The first and second restriction enzyme recognition sites may be the same. At least one of the restriction enzymes may be BpmI, EcoP15I, Bce83I, BsgI, Eco57I, GsuI, MmeI, AloI, BaeI, BcgI, BplI, BsaXI, Bsp24I, CjeI, FalI, PpiI, or PsrI. The target polynucleotide sequence may be an antibody variable region or an antibody hypervariable region. The first and second primers may specifically hybridize to a region flanking an antibody variable region or to a region flanking the antibody hypervariable region. A region flanking another region may be directly adjacent to the other region or may be separated from the other region.

Other embodiments and advantages of the present invention will be apparent from the detailed description that follows.

DETAILED DESCRIPTION OF THE INVENTION

I. Introduction

Figure 1:
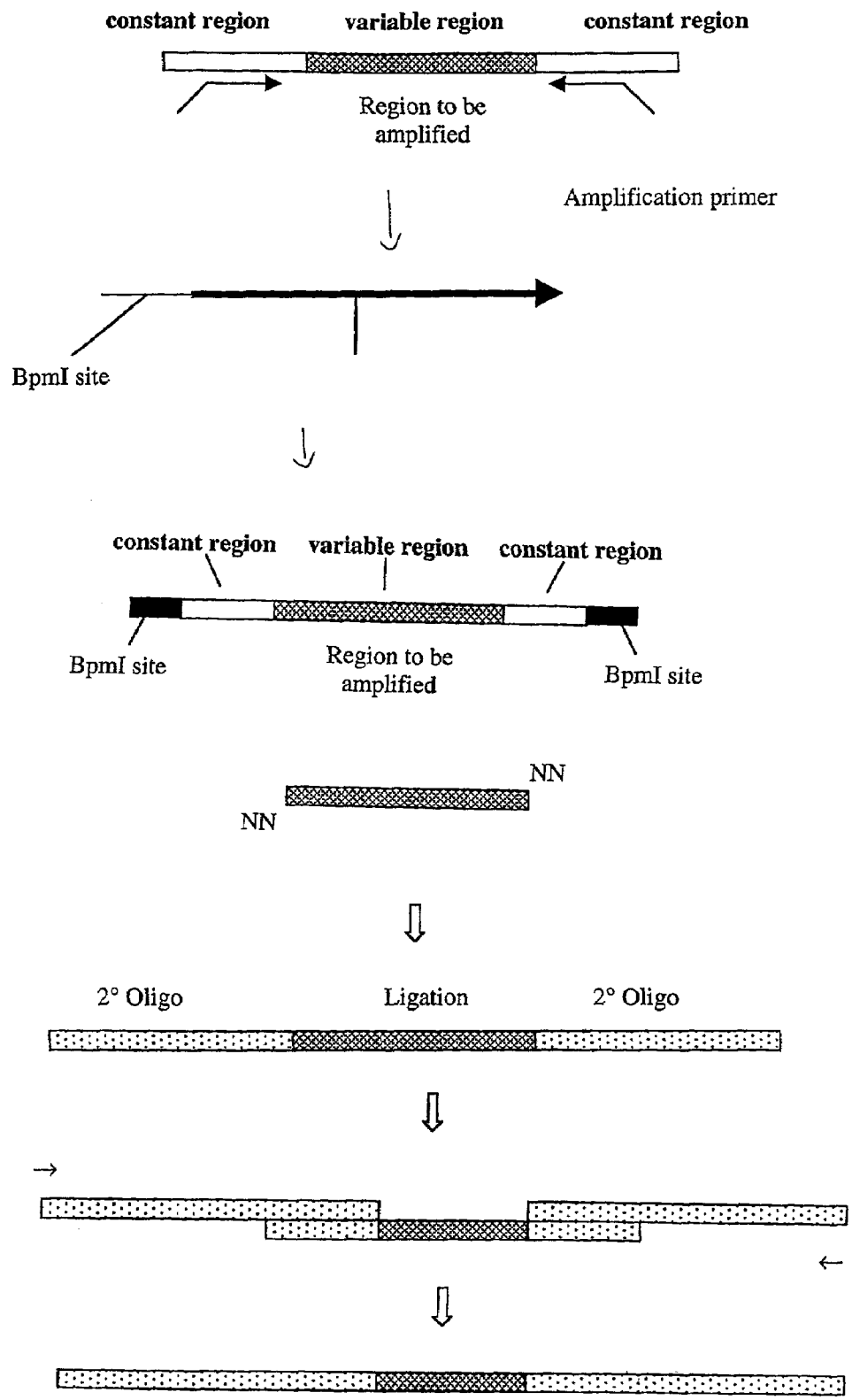
FIG. 1 illustrates the amplification strategy of the present invention.

The present invention provides a method of amplifying target sequences without including regions flanking the target sequence in the amplified product or imposing primer sequences on the amplified product.

The present invention is based on the discovery that restriction enzymes which have a non-panlindromic recognition site and cut at a distance outside of the recognition site can be useful for amplifying a target sequence without including regions flanking the target sequence in the amplified product or imposing primer sequences on the amplified product.

This invention relies on routine techniques in the field of recombinant genetics. Basic texts disclosing the general methods of use in this invention include Sambrook et al., *Molecular Cloning, A Laboratory Manual* (3d ed. 2001); Kriegler, Gene Transfer and Expression: A Laboratory Manual (1990); and *Current Protocols in Molecular Biology* (Ausubel et al., eds., 1994)).

II. Definitions

As used herein, the following terms have the meanings ascribed to them below unless otherwise specified.

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683, 195 and 4,683,202; *PCR Protocols. A Guide to Methods and Applications* (Innis et al., eds, 1990)), strand displacement amplification (SDA) (Walker, et al. *Nucleic Acids Res.* 20(7):1691 (1992); Walker *PCR Methods Appl* 3(1):1 (1993)), transcription-mediated amplification (Phyffer, et al., *J. Clin. Microbiol.* 34:834 (1996); Vuorinen, et al., *J. Clin. Microbiol.* 33:1856 (1995)), nucleic acid sequence-based amplification (NASBA) (Compton, *Nature* 350(6313):91 (1991), rolling circle amplification (RCA) (Lisby, *Mol. Biotechnol.* 12(1):75 (1999)); Hatch et al., *Genet. Anal.*

15(2):35 (1999)) and branched DNA signal amplification (bDNA) (see, e.g., Iqbal et al., *Mol. Cell Probes* 13(4):315 (1999)).

"Amplifying" refers to submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification Teaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 25 nucleotides. The "integrity" of a primer refers to the ability of the primer to primer an amplification reaction. For example, the integrity of a primer is typically no longer intact after degradation of the primer sequences such as by endonuclease cleavage.

A "probe" refers to a polynucleotide sequence capable of hybridization to a polynucleotide sequence of interest and allows for the detecting of the polynucleotide sequence of choice. For example, "probes" can comprise polynucleotides linked to fluorescent or radioactive reagents, thereby allowing for the detection of these reagents.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

The phrase "nucleic acid" or "polynucleotide" refers to deoxyribonucleotides or bonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Two nucleic acid sequences or polypeptides are said to be "identical" if the sequence of nucleotides or amino acid residues, respectively, in the two sequences is the same when aligned for maximum correspondence as described below. The term "complementary to" is used herein to mean all of a first sequence is complementary to at least a portion of a reference polynucleotide sequence.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. The percent identity between two sequences can be represented by any integer from 25% to 100%. More preferred embodiments include at least: 25%, 30%, 35%, 40%, 45%, 50%, 55%, 60%, 65%, 70%, 75%, 80%, 85%, 90%, 95%, or 99%.

One example of an algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Mixed nucleotides are designated as described in e.g. *Eur. J. Biochem.* (1985) 150:1.

"Heterologous", when used with reference to portions of a protein, indicates that the protein comprises two or more domains that are not found in the same relationship to each other in nature. Such a protein, e.g., a fusion protein or a conjugate protein, contains two or more domains from unrelated proteins arranged to make a new functional protein. Heterologous may also refer to a natural protein when it is found or expressed in an unnatural location such as when a mammalian protein is expressed in a bacterial cell. A heterologous polypeptide may correspond to a single known protein (e.g. GFP) or may itself be a heterologous protein composed of domains or portions of multiple different proteins.

"Homologous", when used with reference to portions of a protein, indicates that the protein comprises two or more domains that are found in the same relationship to each other in nature (e.g. antibody hypervariable regions and antibody framework regions). A homologous protein may correspond to one or more domain or portion of single known protein arranged in their native order or rearranged.

A "recombination site" is a nucleotide site at which DNA molecules are cleaved and the fragments are rejoined to give new combinations. The recombination sites may be naturally occurring or may be introduced into the nucleotide sequence using recombinant DNA techniques known to those of skill in the art. Such techniques are described in e.g., Sambrook et al., supra and Ausubel et al., supra.

"Restriction endonuclease" or "restriction enzyme" are used interchangeable to refer to any of a group of enzymes, produced by bacteria, that recognize specific nucleotide sequences ("recognition sites") and cleave molecules of DNA at the recognition site or at a distance from the recognition site. A restriction enzyme recognition site is the specific nucleotide sequence to which a restriction enzyme binds prior to cutting DNA.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition, i.e., the antibody variable region. The terms variable light chain (VL) and variable heavy chain (VH) refer to these light and heavy chains respectively. The antibody variable region comprises three antibody hypervariable regions (also known as complementarity determining regions (CDR's)) and four antibody "framework regions" which flank the CDR's and are conserved. (See, *Fundamental Immunology* (Paul ed., 3d ed. 1993).

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see, *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

A "display vector" refers to a vector used to create a cell or virus that displays, i.e., expresses a display protein comprising a heterologous polypeptide, on its surface or in a cell compartment such that the polypeptide is accessible to test binding antigens.

A "display library" refers to a population of "library vehicles," often, but not always, cells or viruses. The "library vehicle" provides both the nucleic acid encoding a peptide as well as the peptide, such that the peptide is available for binding to a target molecule and further, provides a link between the peptide and the nucleic acid sequence that encodes the peptide. Various "library vehicles" are known to those of skill in the art and include vectors such as, for example, phage, phagemids, yeast and other eukaryotic cells, bacteria, and plasmids as well as noncellular library vehicles for in vitro libraries that do not require cells, for example ribosome display libraries or mRNA display libraries, where a physical linkage occurs between the mRNA or cDNA nucleic acid, and the protein encoded by the mRNA or cDNA. Plasmids can also serve as library vehicles when the peptide is fused to a polypeptide which is able to bind to the plasmid.

The term "link" as used herein refers to a physical linkage as well as linkage that occurs by virtue of co-existance within a biological particle, e.g., phage, bacteria, yeast or other eukaryotic cell.

"Physical linkage" refers to any method known in the art for functionally connecting two molecules, including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations. Two molecules may be directly linked or linked through a linker, spacer, or adaptor.

"As used herein, "linker" or "spacer" or "adaptor" refers to a molecule or group of molecules that connects two molecules, such as a binding ligand and a display protein or nucleic acid; or an amplified product and an oligonucleotide and serves to place the two molecules in a preferred configuration.

As used herein "random peptide library" refers to a set of polynucleotide sequences that encodes a set of random peptides, and to the set of random peptides encoded by those polynucleotide sequences, as well as the fusion proteins containing those random peptides.

As used herein, "CDR library" refers to a set of polynucleotide sequences that encode CDR regions and to the set of CDR polypeptide sequences encoded by those polynucleotide sequences, as well as the fusion proteins containing the CDR sequences.

The phrase "specifically (or selectively) binds" to a binding partner, e.g., an antigen, or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antigen binds to a particular protein above background, e.g., at least two times the background ,and does not substantially bind in a significant amount to other proteins present in the sample. Specific binding to an antibody under these conditions may require an antibody that is selected for its specificity for a particular protein. For example, polyclonal antibodies raised to a particular protein or antigen can be selected to obtain only those polyclonal antibodies that are specifically immunoreactive with the antigen, and not with other proteins, except for polymorphic variants, orthologs, and alleles of the protein. This selection may be achieved by subtracting out antibodies that cross-react with the antigen. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A "phage expression vector" or "phagemid" refers to any phage-based recombinant expression system for the purpose of expressing a nucleic acid sequence in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is "in phase" the protein it encodes will be expressed as part of the coat protein. Thus, libraries of nucleic acid sequences, such as a genomic library from a specific cell or chromosome, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn (1996) Curr. Opin. Biotechnol. 7:547–553). See, e.g., description of phage display libraries, below.

III. Amplification of Target Sequence

One embodiment of the present invention provides a method of amplifying target sequences without including nucleic acids flanking the target sequences or imposing primer sequences on the amplified product. Typically the target sequence is a variable sequence flanked by "constant sequences". Although the "constant sequences" may themselves be variable, such variability does not preclude amplification using a pool of primers designed on the basis of an examination of the variability of such constant sequences. Typically the primers comprise a restriction enzyme recognition sites or sequences. Typically, restriction enzyme recognition sequences are about 4, 5, 6, 7 or 8 base pairs in length, and can be palindromic sequences, nonpalindromic sequences, interrupted sequences, or contiguous sequences of nucleotides. Restriction enzymes typically cleave either at or outside their recognition site. Those that cleave outside their recognition sites usually do so in a staggered cut at a site 4, 6, 8, 9, 10, 11, 12, 13, 14, 15, 16 17, 18, 20, 21, 22, 23, or 24 bases from their recognition site, and it is likely that other enzymes cleaving at other distances exist in nature, or can be engineered. Such cleavage may occur on one side or on both sides of the recognition sequence. Suitable restriction enzymes include, for example, AloI, BaeI, Bce83I, BcgI, BplI, BpmI, BsaXI, BsgI, Bsp24I, CjeI, EcoP15I, Eco57I, FalI, GsuI, MmeI, PpiI, and PsrI. In one preferred embodiment, the restriction enzyme is BpmI. In another preferred embodiment, (V gene amplification) the restriction enzyme is BcgI, or a mixture of two enzymes (e.g., MmeI and Bce83I).

Often, the target sequences will be an antibody hypervariable region flanked by framework regions. Preferably the primers comprise a restriction enzyme recognition site for a nonpalindromic restriction enzyme, allowing cleavage of the amplified product downstream of the primer sequence, outside of the primer and within the region of amplification. The methods of the present invention are particularly useful for amplifying antibody hypervariable region sequences free of flanking regions, i.e., CDR regions without framework regions.

A. Reaction Components

1. Oligonucleotide Primers

The oligonucleotides that are used in the present invention as well as oligonucleotides designed to detect amplification products can be chemically synthesized, as described above. These oligonucleotides can be labeled with radioisotopes, chemiluminescent moieties, or fluorescent moieties. Such labels are useful for the characterization and detection of amplification products using the methods and compositions of the present invention.

The primer components may be present in the PCR reaction mixture at a concentration of, e.g., between 0.1 and 1.0 µM. The concentration of the target primers can be from about 0.1 to about 0.75 µM. The primer length can be between, e.g., 15–100 nucleotides in length and preferably have 40–60% G and C composition. In the choice of primer, it is preferable to have exactly matching bases at the 3' end of the primer but this requirement decreases to relatively insignificance at the 5' end. Preferably, the primers of the invention all have approximately the same melting temperature.

Typically, the primers have the following design. The most 3' portion anneals to the constant region flanking the target region to be amplified, this portion will normally have at least 6 bp of homology to the target region, preferably 9 or more bp. The region of homology is adjacent to the restriction enzyme sequence. If this recognition site is an interrupted sequence, the intervening portion of sequence between the two portions of the restriction enzyme site will normally contain bases which can anneal to the appropriate portion of the constant region flanking the target of interest. 5' to the restriction enzyme site are sufficient bases to allow the restriction enzyme to recognize its site and cleave the recognized sequence. Where the restriction enzyme site cleaves twice, once on either side of the recognition site, the primer should be sufficiently long to allow the enzyme to cleave at both of the cleavage sites. The extra nucleotides may or may not have further homology to the constant region flanking the target of interest.

2. Buffer

Buffers that may be employed are borate, phosphate, carbonate, barbital, Tris, etc. based buffers. (See, U.S. Pat. No. 5,508,178). The pH of the reaction should be maintained in the range of about 4.5 to about 9.5. (See, U.S. Pat. No. 5,508,178. The standard buffer used in amplification reactions is a Tris based buffer between 10 and 50 mM with a pH of around 8.3 to 8.8. (See Innis et al., supra.).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

3. Salt Concentration

The concentration of salt present in the reaction can affect the ability of primers to anneal to the target nucleic acid. (See, Innis et al.). Potassium chloride is added up to a concentration of about 50 mM to the reaction mixture to promote primer annealing. Sodium chloride can also be added to promote primer annealing. (See, Innis et al.).

4. Magnesium Ion Concentration

The concentration of magnesium ion in the reaction can affect amplification of the target sequence(s). (See, Innis et al.). Primer annealing, strand denaturation, amplification specificity, primer-dimer formation, and enzyme activity are all examples of parameters that are affected by magnesium concentration. (See, Innis et al.). Amplification reactions should contain about a 0.5 to 2.5 mM magnesium concentration excess over the concentration of cNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

5. Deoxynucleotide Triphosphate Concentration

Deoxynucleotide triphosphates (dNTPs) are added to the reaction to a final concentration of about 20 µM to about 300 µM. Typically, each of the four dNTPs (G, A, C, T) are present at equivalent concentrations. (See, Innis et al.).

6. Nucleic Acid Polymerase

A variety of DNA dependent polymerases are commercially available that will function using the methods and compositions of the present invention. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1–5 units per reaction mixture. The reaction mixture is typically between 20 and 100 µl.

In some embodiments, a "hot start" polymerase can be used to prevent extension of mispriming events as the temperature of a reaction initially increases. Hot start polymerases can have, for example, heat labile adducts requiring a heat activation step (typically 95° C. for approximately 10–15 minutes) or can have an antibody associated with the polymerase to prevent activation.

7. Other Agents

Additional agents are sometime added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction. (See, Innis et al. supra). Stabilizing agents such as gelatin, bovine serum albumin, and non-ionic detergents (e.g. Tween-20) are commonly added to amplification reactions. (See, Innis et al. supra).

B. Amplification

Amplification of an RNA or DNA template using reactions is well known (see, U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal cycler to facilitate incubation times at desired temperatures. Degenerate oligonucleotides can be designed to amplify target DNA sequence homologs using the known sequences that encode the target DNA sequence. Restriction endonuclease sites can be incorporated into the primers. Polymerase chain reaction or other in vitro amplification methods may also be useful, for example, to clone nucleic acid sequences that code for the target DNA sequence proteins to be expressed. Genes amplified by the PCR reaction can be purified from agarose gels and cloned into an appropriate vector.

Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

Isothermic amplification reactions are also known and can be used according to the methods of the invention. Examples of isothermic amplification reactions include strand displacement amplification (SDA) (Walker, et al. *Nucleic Acids*

Res. 20(7):1691 (1992); Walker *PCR Methods Appl* 3(1):1 (1993)), transcription-mediated amplification (Phyffer, et al., *J. Clin. Microbiol.* 34:834 (1996); Vuorinen, et al., *J. Clin. Microbiol.* 33:1856 (1995)), nucleic acid sequence-based amplification (NASBA) (Compton, *Nature* 350(6313):91 (1991), rolling circle amplification (RCA) (Lisby, *Mol. Biotechnol.* 12(1):75 (1999)); Hatch et al., *Genet. Anal.* 15(2):35 (1999)) and branched DNA signal amplification (bDNA) (see, e.g., Iqbal et al., *Mol Cell Probes* 13(4):315 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS (hybrid capture system). Any amplification method known to those of skill in the art may be used with the methods of the present invention provided two primers are present at either end of the target sequence, and these primers contain a restriction site which cuts in the variable region, outside of the primers sequence C. Expression in Prokaryotes and Eukaryotes Once desired target sequences are identified, the polypeptides of interest can be expressed in prokaryotes and eukaryotes. To obtain high level expression of a cloned nucleotide sequence, such as those cDNAs encoding a protein of interest, one typically subclones a nucleic acid sequence encoding the protein of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein of interest are available in, e.g., *E. coli, Bacillus* sp., and *Salmonella* (Palva et al., *Gene* 22:229 (1983); Mosbach et al., *Nature* 302:543 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the protein encoding nucleic acid in host cells. A typical expression cassette thus contains a promoter operably linked to the nucleic acid sequence encoding the protein of interest and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *Proc. Natl. Acad. Sci.* 89:5547 (1992); Oligino et al., *Gene Ther.* 5:491 (1998); Wang et al., *Gene Ther.* 4:432–441 (1997); Neering et al., *Blood* 88:1147 (1996); and Rendahl et al., *Nat. Biotechnol.* 16:757 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of the fusion protein, which is then purified using standard techniques (see, e.g., Colley et al., *J. Biol. Chem.* 264:17619 (1989); *Guide to Protein Purification*, in

*Methods in Enzymology*, v. 182 (Deutscher, ed., 1990)). Transformation of eukaryotic and prokaryotic cells are performed according to standard techniques (see, e.g., Morrison, *J. Bact.* 132:349 (1977); Clark-Curtiss & Curtiss, *Methods in Enzymology* 101:347 (see, Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of interest.

After the expression vector is introduced into the cells, the transfected cells are cultured under conditions favoring expression of the protein of interest, which is recovered from the culture using standard techniques known in the art.

IV. Libraries

A. Library Construction

Another embodiment of the invention provides a method of preparing a library. The library may comprise amplified target sequences that include neither nucleic acids flanking the target sequences nor primer sequences, e.g., antibody hypervariable regions free of framework regions, or pure antibody variable regions free of flanking constant or leader sequences. Other genes, such as T cell receptor genes, which exist in a diversity of different forms, may also be isolated as a library using the methods of the present invention. Alternatively, the library may comprise an amplified product linked to a homologous or heterologous protein or a portion thereof, i.e., fusion proteins, as described below. The amplified product may be fused to a recombination site, or to a restriction endonuclease site. Libraries comprising target sequences amplified using the methods of the present invention can be screened to select for specific variable regions with particular binding affinities. Methods of preparing and screening libraries are described in e.g., Sambrook et al., supra.

Methods of generating displayed peptides and antibodies are also described in U.S. Pat. No. 5,830,721. Peptide sequences, antibodies, or other proteins can be displayed on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member. The present invention provides methods to generate nucleic acid sequences encoding the polypeptides displayed using cell or virus based systems as well as in vitro systems such as, for example, ribosome display and mRNA display.

Ligand binding libraries can be constructed using a number of different display systems. In cell or virus-based systems, the ligand can be displayed, for example, on the surface of a particle, e.g., a virus or cell and screened for the ability to interact with other molecules, e.g., a library of antibodies. In vitro display systems, in which the binding ligand is linked to an agent that provides a mechanism for coupling the binding ligand to the nucleic acid sequence that encodes it, can also be used.

WO 93/08278 describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s). The present invention provides methods to generate nucleic acid sequences encoding the polypeptides which can be fused to the DNA binding proteins.

As noted above, in some instances, for example, ribosomal display, a binding ligand is linked to the nucleic acid sequence through a physical interaction, for example, with a ribosome. In other embodiments, e.g., mRNA display, the binding ligand may be joined to another molecule via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similar linking group. Other near neutral amino acids, such as Ser can also be used in the linker sequence. Amino acid sequences which may be usefully employed as linkers include those disclosed in Maratea et al. (1985) *Gene* 40:39; Murphy et al. (1986) *Proc. Natl. Acad. Sci. USA* 83:8258; U.S. Pat. Nos. 4,935,233 and 4,751,180. The linker sequence may generally be from 1 to about 50 amino acids in length, e.g., 2, 3, 4, 6, or 10 amino acids in length, but can be 100 or 200 amino acids in length.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold (1990) *Science* 249: 505; Ellington and Szostak, (1990) *Nature* 346: 818). A similar technique was used to identify DNA sequences which bind a predetermined human transcription factor (Thiesen and Bach, (1990) *Nucleic Acids Res.* 18: 3203; Beaudry and Joyce, (1992) *Science* 257; 635; WO 92/05258 and WO 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in WO 88/08453; WO 90/05785; WO 90/07003; WO 91/02076; WO 91/05058; and WO 92/02536.

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence, such as CDRs, V genes, reassembled antibody or antibody fragment genes, or any other libraries of variable gene sequences which can be harvested using this method.

Combinatorial libraries of antibodies have been generated in bacteriophage lambda expression systems which may be screened as bacteriophage plaques or as colonies of lysogens (Huse et al. (1989) *Science* 246: 1275; Caton and Koprowski, (1990) *Proc. Natl. Acad. Sci. USA* 87: 6450; Mullinax et al., (1990) *Proc. Natl. Acad. Sci. USA* 87: 8095; Persson et al., (1991) *Proc. Natl. Acad. Sci. USA* 88: 2432). Various embodiments of bacteriophage antibody display libraries and lambda phage expression libraries have been described (Kang et al., *Proc. Natl. Acad. Sci. USA* 88: 4363 (1991); Clackson et al., *Nature* 352: 624 (1991); McCafferty et al. (1990) Nature 348: 552; Burton et al., *Proc. Natl. Acad. Sci. USA* 88: 10134 (1991); Hoogenboom et al., *Nucleic Acids Res.* 19: 4133 (1991); Chang et al., *J. Immunol.* 147: 3610 (1991); Breitling et al., *Gene* 104: 147 (1991); Marks et al., *J. Mol. Biol.* 222: 581 (1991); Barbas et al., *Proc. Natl. Acad. Sci. USA* 89: 4457 (1992); Hawkins and Winter, *J. Immunol.* 22: 867 (1992); Marks et al., *Biotechnology* 10: 779 (1992); Marks et al., *J. Biol. Chem.* 267: 16007 (1992); Lowman et al, *Biochemistry* 30: 10832 (1991); Lerner et al., *Science* 258: 1313 (1992)). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts). Generally the source of such antibody libraries has been either synthetic antibody genes, or antibody genes generated by V region PCR. In the latter case, the use of primers annealing to the V regions can change the V region sequences and the properties of the encoded antibody in a detrimental fashion. The methods of the present invention ensure that the sequences of the variable or hypervariable (CDR) regions which are used in such display libraries are identical or substantially identical to those in the original source material.

1. Phage Display Libraries

Construction of phage display libraries exploits the bacteriophage's ability to display peptides and proteins on their surfaces, i.e., on their capsids. Often, filamentous phage such as M13 or fl are used. Filamentous phage contain single-stranded DNA surrounded by multiple copies of genes encoding major and minor coat proteins, e.g., pIII. Coat proteins are displayed on the capsid's outer surface. DNA sequences inserted in-frame with capsid protein genes are co-transcribed to generate fusion proteins or protein fragments displayed on the phage surface. Phage libraries thus can display peptides representative of the diversity of the inserted sequences. Significantly, these peptides can be displayed in "natural" folded conformations. The binding ligands expressed on phage display libraries can then bind target molecules, i.e., they can specifically interact with binding partner molecules such as antigens, e.g., (Petersen (1995) *Mol. Gen. Genet.* 249:425), cell surface receptors (Kay (1993) *Gene* 128:59), and extracellular and intracellular proteins (Gram (1993) *J. Immunol. Methods* 161:169).

The concept of using filamentous phages, such as M13 or fd, for displaying peptides on phage capsid surfaces was first introduced by Smith (1985) *Science* 228:1315. Peptides have been displayed on phage surfaces to identify many potential ligands (see, e.g., Cwirla (1990) *Proc. Natl. Acad. Sci. USA* 87:6378). There are numerous systems and methods for generating phage display libraries described in the scientific and patent literature, see, e.g., Sambrook, et al., supra; "Phage Display of Peptides and Proteins: A Laboratory Manual, Academic Press, San Diego, 1996; Crameri (1994) *Eur. J. Biochem.* 226:53; de Kruif (1995) *Proc. Natl. Acad. Sci. USA* 92:3938; McGregor (1996) *Mol Biotechnol.* 6:155; Jacobsson (1996) *Biotechniques* 20:1070; Jespers (1996) *Gene* 173:179; Jacobsson (1997) *Microbiol Res.* 152:121; Fack (1997) *J. Immunol. Methods* 206:43; Rossenu (1997) *J. Protein Chem.* 16:499; Katz (1997) *Annu. Rev. Biophys. Biomol. Struct.* 26:27; Rader (1997) *Curr. Opin. Biotechnol.* 8:503; Griffiths (1998) *Curr. Opin. Biotechnol.* 9:102.

Typically, exogenous nucleic acids encoding the protein sequences to be displayed are inserted into a coat protein gene, e.g. gene III or gene VIII of the phage. The resultant fusion proteins are displayed on the surface of the capsid. Protein VIII is present in approximately 2700 copies per phage, compared to 3 to 5 copies for protein III (Jacobsson (1996), supra). Multivalent expression vectors, such as phagemids, can be used for manipulation of the nucleic acid sequences encoding the binding library and production of phage particles in bacteria (see, e.g., Felici (1991) *J. Mol. Biol.* 222:301).

Phagemid vectors are often employed for constructing the phage library. These vectors include the origin of DNA replication from the genome of a single-stranded filamentous bacteriophage, e.g., M13 or fl and require the supply of the other phage proteins to create a phage. This is usually supplied by a helper phage which is less efficient at being packaged into phage particles. A phagemid can be used in the same way as an orthodox plasmid vector, but can also be used to produce filamentous bacteriophage particle that contain single-stranded copies of cloned segments of DNA.

The displayed protein does not need to be a fusion protein. For example, a binding ligand may attach to a coat protein by virtue of a non-covalent interaction, e.g., a coiled coil binding interaction, such as jun/fos binding, or a covalent interaction mediated by cysteines (see, e.g., Crameri et al., (1994) *Eur. J. Biochem.* 226:53) with or without additional non-covalent interactions. Morphosys have described a display system in which one cysteine is put at the C terminus of the scFv or Fab, and another is put at the N terminus of g3p. The two assemble in the periplasm and display occurs without a fusion gene or protein.

The coat protein does not need to be endogenous. For example, DNA binding proteins can be incorporated into the phage/phagemid genome (see, e.g., McGregor & Robins, *Anal. Biochem.* 294:108–117, 2001). When the sequence recognized by such proteins is also present in the genome, the DNA binding protein becomes incorporated into the phage/phagemid. This can serve as a display vector protein. In some cases it has been shown that incorporation of DNA binding proteins into the phage coat can occur independently of the presence of the recognized DNA signal.

Other phage can also be used. For example, T2, T4, T7 vectors or lambda vectors can be employed in which the displayed product on the mature phage particle is released by cell lysis.

Another methodology is selectively infective phage (SIP) technology. which provides for the in vivo selection of interacting protein-ligand pairs. A "selectively infective phage" consists of two independent components. For example, a recombinant filamentous phage particle is made non-infective by replacing its N-terminal domains of gene 3 protein (g3p) with a protein of interest, e.g., an antigen. The nucleic acid encoding the antigen can be inserted such that it will be expressed. The second component is an "adapter" molecule in which the ligand is linked to those N-terminal domains of g3p that are missing from the phage particle. Infectivity is restored when the displayed protein (e.g., a binding ligand) binds to the antigen. This interaction attaches the missing N-terminal domains of g3p to the phage display particle. Phage propagation becomes strictly dependent on the protein-ligand interaction. See, e.g., Spada (1997) *J. Biol. Chem.* 378:445; Pedrazzi (1997) *FEBS Lett.* 415:289; Hennecke (1998) *Protein Eng.* 11:405.

2. Other Display Libraries

In addition to phage display libraries, analogous epitope display libraries can also be used. For example, the methods of the invention can also use yeast surface displayed libraries (see, e.g., Boder, (1997) *Nat. Biotechnol.* 15:553), which can be constructed using such vectors as the pYD1 yeast expression vector. Other potential display systems include mammalian display vectors and *E. coli* libraries. For example, the *E. coli* flagellin protein can be used to display binding ligand sequences.

In vitro display library formats known to those of skill in the art can also be used, e.g., ribosome displays libraries and mRNA display libraries. In these in vitro selection technologies, proteins are made using cell-free translation and physically linked to their encoding mRNA after in vitro translation. In typical methodology for generating these libraries, DNA encoding the sequences to be selected are transcribed in vitro and translated in a cell-free system.

In ribosome display library (see, e.g., Mattheakis et al., (1994) *Proc. Natl. Acad. Sci USA* 91:9022; Hanes & Pluckthun, (1997) *Proc. Natl. Acad. Sci USA* 94:4937) the link between the mRNA encoding the binding ligand of the invention and the ligand is the ribosome itself. The DNA construct is designed so that no stop codon is included in the transcribed mRNA. Thus, the translating ribosome stalls at the end of the mRNA and the encoded protein is not released. The encoded protein can fold into its correct structure while attached to the ribosome. The complex of mRNA, ribosome and protein is then directly used for selection against an immobilized target. The mRNA from bound ribosomal complexes is recovered by dissociation of the complexes with EDTA and amplified by RT-PCR.

Method and libraries based on mRNA display technology, also referred to herein as puromycin display, are described, for example in U.S. Pat. Nos. 6,261,804; 6,281,223; 6,207,446; and 6,214,553. In this technology, a DNA linker attached to puromycin is first fused to the 3' end of mRNA. The protein is then translated in vitro and the ribosome stalls at the RNA-DNA junction. The puromycin, which mimics aminoacyl tRNA, enters the ribosomal A site and accepts the nascent polypeptide. The translated protein is thus covalently linked to its encoding mRNA. The fused molecules can then be purified and screened for binding activity. The nucleic acid sequences encoding ligands with binding activity can then be obtained, for example, using RT-PCR.

The binding ligand and sequences, e.g., DNA linker for conjugation to puromycin, can be joined by methods well known to those of skill in the art and are described, for example, in U.S. Pat. Nos. 6,261,804; 6,281,223; 6,207,446; and 6,214,553.

Other technologies involve the use of viral proteins (e.g., protein A) that covalently attach themselves to the genes that encode them. Fusion proteins are created that join the binding ligand to the protein A sequence, thereby providing a mechanims to attached the binding ligands to the genes that encode them.

Plasmid display systems rely on the fusion of displayed proteins to DNA binding proteins, such as the lac repressor (see, e.g., Gates et al., (1996) *J. Mol. Biol.* 255:373; *Methods Enzymol.* 267:171, 1996). When the lac operator is present in the plasmid as well, the DNA binding protein binds to it and can be copurified with the plasmid. Libraries can be created linked to the DNA binding protein, and screened upon lysis of the bacteria. The desired plasmid/proteins are rescued by transfection, or amplification.

B. Screening Libraries

Methods of screening the libraries of the invention are well known to those in the art. The libraries are typically screened using an antigen, or molecule of interest, for which it is desirable to select a binding partner. Typically, the antigen is attached to a solid surface or a specific tag, such as biotin. The antigen (or molecule of interest) is incubated with a library of the invention. Those polypeptides that bind to the antigen are then separated from those that do not using any of a number of different methods. These methods involve washing steps, followed by elution steps. Washing can be done, for example, with PBS, or detergent-containing buffers. Elution can be performed with a number of agents, depending on the type of library. For example, an acid, a base, bacteria, or a protease can be used when the library is a phage display library.

If the library that is being screened is one in which many copies of the binding ligand are displayed on the surface of an organism (e.g., yeast or bacteria), selection can be carried out by labeling the target with a fluorescent marker (such as fluorescein) and sorting those organisms which exhibit a higher fluorescence, by virtue of their increased binding to the target.

To facilitate the identification and isolation of the antigen-bound ligand, the binding ligand can also be engineered as a fusion protein to include selection markers (e.g., epitope tags). Antibodies reactive with the selection tags present in the fusion proteins or moieties that bind to the labels can then be used to isolate the antigen/binding ligand complex via the epitope or label. For example, binding ligand/antigen complexes can be separated from non-complexed display particle using antibodies specific for the antibody selection "tag" e.g., an SV5 antibody specific to an SV5 tag. In libraries that are constructed using a display vector, such as a phage display vector, the selected clones, e.g., phage, are then used to infect bacteria.

Other detection and purification facilitating domains include, e.g., metal chelating peptides such as polyhistidine tracts and histidine-tryptophan modules that allow purification on immobilized metals, protein A domains that allow purification on immobilized immunoglobulin, or the domain utilized in the FLAGS extension/affinity purification system (Immunex Con, Seattle Wash.). Any epitope with a corresponding high affinity antibody can be used, e.g., a myc tag (see, e.g., Kieke (1997) *Protein Eng.* 10:1303–1310) or an E-tag (Pharmacia). See also Maier (1998) *Anal. Biochem.* 259:68–73; Muller (1998) *Anal. Biochem.* 259:54–61. The inclusion of a cleavable linker sequences such as Factor Xa or enterokinase (Invitrogen, San Diego Calif.) between the purification domain and binding site may be useful to facilitate purification. For example, an expression vector of the invention includes a polypeptide-encoding nucleic acid sequence linked to six histidine residues. A widely used tag is six consecutive histidine residues or 6His tag (SEQ ID NO:66). These residues bind with high affinity to metal ions immobilized on chelating resins even in the presence of denaturing agents and can be mildly eluted with imidazole. Selection tags can also make the epitope or binding partner (e.g., antibody) detectable or easily isolated by incorporation of, e.g., predetermined polypeptide epitopes recognized by a secondary reporter/binding molecule, e.g., leucine zipper pair sequences; binding sites for secondary antibodies; transcriptional activator polypeptides; and other selection tag binding compositions. See also, e.g., Williams (1995) *Biochemistry* 34:1787–1797.

The screening protocols typically employ multiple rounds of selection to identify a binding ligand with the desired properties. For example, it may be desirable to select binding ligands with a minimum binding avidity for a target. Alternatively, a maximum binding avidity of a target may be desirable. In other uses, it may be desirable to select a binding ligand that is thermostable at a particular temperature. For example, selection using increasingly stringent binding conditions can be used to select binding ligands that bind to a target molecule at increasingly greater binding affinities. One method of performing this selection is by decreasing concentrations of an antigen to select binding ligands from a library that have a higher affinity for the antigen. A variety of other parameters can also be adjusted to select for high affinity binding ligands, e.g., increasing salt concentration, temperature, and the like.

Once a ligand is selected, the nucleic acid encoding the ligand is readily obtained. This sequence may then be expressed using any of a number of systems to obtain the desired quantities of the protein. There are many expression systems for that are well know to those of ordinary skill in the art. (See, e.g., *Gene Expression Systems*, Fernandes and Hoeffler, Eds. Academic Press, 1999; Ausubel, supra.) Typically, the polynucleotide that encodes the binding ligand is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

V. Fusion Proteins

The methods of the present invention can conveniently be used to generate fusion proteins between the amplified product and homologous or heterologous proteins. The amplified product may be inserted into a single site within the homologous or heterologous polypeptide. The amplified product may be inserted into more than one site within the homologous or heterologous polypeptide, for example to produce a hybrid protein gene. The amplified product may be inserted at or near a homologous site within a homologous polypeptide. The amplified products may be inserted into any site or any number of sites (e.g., at least 2, 3, or 4 sites) within any homologous or heterologous polypeptide. The amplified products may further be modified by the addition of sequences which permit in vitro transcription and translation of the polypeptides. The methods of the present invention are particularly useful for generating fusion proteins comprising antibody hypervariable regions free of flanking regions, i.e., framework regions. In a preferred embodiment, fusion proteins that can be constructed according to the methods of the present invention include, for example, amplified variable regions fused to regions which are constant (I want to avoid the possibility of confusion with antibody constant regions). Suitable variable regions include, for example, antibody variable regions and antibody hypervariable regions. Suitable constant regions include, for example, antibody framework regions, polypeptides which can be used for display purposes, any scaffold protein containing at its surface a loop, or loops, into which such variable regions can be inserted. An exemplary fusion protein is, for example, antibody hypervariable region-fluorescent protein (i.e., a fluorobody). In a particularly preferred embodiment, the fluorescent protein is green fluorescent protein (GFP). In another preferred embodiment, the amplified antibody hypervariable region products are inserted into sites within 5 amino acids of either side of amino acid positions of 23, 101, 171, 213 of GFP.

EXAMPLES

The following examples are offered to illustrate, but not to limit the claimed invention.

Example 1

CDR3 Regions for a Fluorobody Library

This example demonstrates the generation of CDR3 sequences to be included in a fluorobody library.

In order to amplify all possible CDR3 sequences, degenerate forward or reverse primers (Table 1) were designed from an examination of the germ line sequences in V-Base. A BpmI restriction site and biotin were added to the 5' end of each primer. Human cDNA prepared from naïve lymphocytes using random hexamer primers was used as a template for PCR using all the primers in Table 1 together. 1 µl of template was amplified by PCR in 50 µl of reaction buffer containing 10 mM KCl, 20 mM Tris-HCl, pH 8.8, 2 mM MgSO4, 10 mM (NH2)$_4$SO4, 0.1% Triton X-100, 2 U of Vent Polymerase, and 0.2 mM dNTPs using following conditions: 94° C. for 2 min, then 30 cycles of 94° C. for 30 sec, 60° C. for 30 sec, and 72° C. for 45 sec. Amplification was completed with a 10 min incubation at 72° C.

PCR products were separated in a 4% Metaphor gel (BMA, Rockland, Me.) and the population of CDR3 (ranging in size from about 75 bp to about 150 bp including primer sequences) was excised from the gel and cleaned with a gel extraction kit (Qiagen, Valencia Calif.). For all PCR amplifications, Vent, a non-error prone DNA Polymerase (New England Biolabs (NEB), Beverly Mass.) was used. This amplification protocol produced CDR3s flanked at either end by BpmI sites and Biotin.

TABLE 1

Primer sequences to amplify V<sub>H</sub> CDR3 sequences:

| | |
|---|---|
| VR35-1 | 5'Biotin-CGTG CTGGAG TAT TAC TGT GCR AGA GA  (SEQ ID NO:1) |
| VR35-2 | 5'Biotin-CGTG CTGGAG TAT TAC TAT GCG AGA GA  (SEQ ID NO:2) |
| VR35-3 | 5'Biotin-CGTG CTGGAG TAT TAC TGT GCR RCA GA  (SEQ ID NO:3) |
| VR35-4 | 5'Biotin-CGTG CTGGAG TAT TAC TGT ACC ACA GA  (SEQ ID NO:4) |
| VR35-5 | 5'Biotin-CGTG CTGGAG TAT TAC TGT RCY AGA GA  (SEQ ID NO:5) |
| VR35-6 | 5'Biotin-TKTG CTGGAG TAT TAC TGT GCR AAA GA  (SEQ ID NO:6) |
| VR35-7 | 5'Biotin-TGTG CTGGAG TAT TAC TGT AAG AAA GA  (SEQ ID NO:7) |
| VR35-8 | 5'Biotin-CGTG CTGGAG TAT TAC TGT GCG AGA GG  (SEQ ID NO:8) |
| VR33-1 | 5'Biotin-CRGT CTGGAG GAC CAG GGT GCC CYG GCC (SEQ ID NO:9) |
| VR33-2 | 5'Biotin-CGGT CTGGAG GAC CAT TGT CCC TTG GCC (SEQ ID NO:10) |
| VR33-3 | 5'Biotin-CGGT CTGGAG GAC CAG GGT TCC TTG GCC (SEQ ID NO:11) |
| VR33-4 | 5'Biotin-CGGT CTGGAG GAC CGT GGT CCC TTG GCC (SEQ ID NO:12) |

This CDR3 population was then digested with BpmI (NEB, Beverly Mass.) at 37° C. overnight. Primer sequences conjugated to biotin were released by this digestion and removed by incubation with streptavidin magnetic beads (Dynal, Oslo Norway) for 1.5 hour at room temperature with mixing every 10 min. The beads with attached cleaved primer sequences were removed by drawing to one side in a magnetic rack, and removing the supernatant which contains the CDR3s in solution with no attached primer sequence. As BpmI cleaves to leave a 2 bp overhang at a defined distance from its recognition site, and the primers were designed to amplify the conserved region around the highly variable CDR3, the sequence of these 2 bp overhangs, which are found at the beginning of the CDR3, was known. The expected overhang sequences are:

```
5' CDR3-CC 3' and

3' TC-CDR3 5'
```

In order to amplify these CDR3 sequences and insert them into defined loops in GFP, adaptors were ligated to each end of the CDR3 sequences, making use of the defined overhangs described above. The adaptors consisted of portions of the GFP sequence flanking the chosen loops with the required overhangs for ligation to the CDRs. Table 2 shows the oligonucleotides representing sense or antisense of the GFP loops. Adaptor sequences are provided in the table, with the overhangs used to ligate to the CDR3 underlined and in bold. The adaptors are used in pairs as described below. One of each pair also has an overhang at the other end, designed to prevent linker ligation.

TABLE 2 adaptor sequences (SEQ ID NOS:13–28)

Adaptor 1 (GFP 4–22)*:
5'-GGAGAAGAACTTTTCACTGGAGTTGTCCCAATTCTTGTTGAATTAGATGGTGATGTTAG#-3'

3'-CCTCTTCTTGAAAAGTGACCTCAACAGGGTTAAGAACAACTTAATCTACCACTACAA-P

Adaptor 2 (GFP 24–42):
5'P-    GGGCACAAATTTTCTGTCAGAGGAGAGGGTGAAGGTGATGCTACAACGGAAAAC -3'

3'- GGCCCGTGTTTAAAAGACAGTCTCCTCTCCGACTTCCACTACGATGTTGCCTTTTGAG-5'

Adaptor 3 (GFP 85–102):
5'- AAGAGTGCCATGCCCGAAGGTTATGTACAGGAACGCACTATATCTTTCAAAGATAG-3'

3'- TTCTCACGGTA GGGCTTCCAATACATGTCCTTGCGTGATATAGAAAGTTTCTA-P-5'

Adaptor 4 (GFP 103–120):
5'-P- GACGGGACCTACAAGACGCGTGCTGAAGTCAAGTTTGAAGGTGATACCCTTG-3'

3'- GGCTGCCCTGGATGTTCTGCGCACGACTTCAGTTCAAACTTCCACTATGGGAACAA 5'

TABLE 2-continued adaptor sequences (SEQ ID NOS:13-28)

Adaptor 5 (GFP 163-172):
5'-CAAAAGAATGGAATCAAAGCTAACTTCAAAATTCGCCACAACGTTGAAG-3'

3'-TTTCTTACCTTAGTTTCGATTGAAGTTTTAAGCGGTGTTGCTTCT-P-5'

Adaptor 6 (GFP 173-184):
5'-P-GATGGTTCCGTTCAACTAGCAGACCATTATCAACAAAATACTCCAAT-3'

3'-GGCTACCAAGGCAAGTTGATCGTCTGGTAATAGTTGTTTTATGAGGTTAAC-5'

Adaptor 7 (GFP 192-213):
5'-CCTGTCCTTTTACCAGACAACCATTACCTGTCGACACAATCTGTCCTTTCGAAAGATCCCAACGAAG-3'

3'-GGACAGGAAAATGGTCTGTTGGTAATGGACAGCTGTGTTAGACAGGAAAGCTTTCTAGGGTTGCT--P-5'

Adaptor 8 (GFP 214-235):
5'- P- AAGCGTGACCACATGGTCCTTCTTGAGTTTGTAACTGCTGCTGGGATTACACATGGCATGGATG-3'

3'- GGTTCGCACTGGTGTACCAGGAAGAACTCAAACATTGACGACGACCCTAATGTGTACCGTACCTACTC- 5'

*Numbers represent amino acid sequences of superfolder GFP.
Overhang nucleotides for ligation (Bold and underlined).

The 60-66 nucleotide length oligos representing sense or antisense strand of each side of the GFP loops were synthesized (Operon, Richmond, Calif.) and the 5' site of sense of one side and antisense of the other side were phosphorylated (Table 2) so that the adaptors could ligate to the CDR3s. The oligonucleotides corresponding to each adaptor pair were mixed at 3 μm final concentration in 50 μl volume of NEB Buffer 2 (10 mM Tris-HCl, pH 7.9, 10 mM MgCl$_2$, 50 mM NaCl$_2$, and 1 mM dithiothreitol) and heated at 97° C. for 7 min to completely denature and then gradually cooled to 25° C. An aliquot of the annealed adaptor was run on a 4% metaphor gel to confirm the completion of annealing. The double-stranded oligos were mixed with the BpmI-digested CDR3 population in the presence of 40 U T4 DNA ligase and incubated at 15° C. for 16 hours in 20 μl volume of buffercontaining 50 mM Tris-HCl, pH 7.5, 10 mM MgCl$_2$, 10 mM DTT, 1 mM ATP, and 25 μg/ml BSA. One microliter of CDR3-GFP chimeras were further amplified using same but non-phosphorylated, oligos as primers. After these amplifications, the following fragments were created:

Example 2

Creation of an Unmodified V$_H$ Gene Library

This example demonstrates the generation of V$_H$ sequences for a library.

To isolate V$_H$ genes from lymphocyte cDNA without imposing any primer sequences upon the amplified V$_H$ genes, primers which anneal in the V$_H$ leader regions and in the CR1 constant region were used. Primer sequences for either IgG or IgM are given, but similar primers can also be designed for IgA, IgD or IgB. The primers all have the following features:

(1) they anneal to either V$_H$ leader or CH1 sequences close to, but not adjacent to, the V$_H$ gene itself;
(2) each primer contains a BcgI site (indicated in red). BcgI upon recognizing its site cleaves DNA twice, once on either side of the recognition site, to leave a 2 bp 3' overhang at either end of the cleaved DNA (10/12 bp from the site). BcgI does not cut in any V, D or J gene.

TABLE 3

Ligation CDR3 to oligos of GFP loops and amplification of ligated products:

| | Assembled from fragments | | | Amplified with | |
|---|---|---|---|---|---|
| Fragment name | Fragment 1 | Fragment 2 | Fragment 3 | 5' primer | 3' primer |
| GFP/CDR3.1 | Adaptor 1 (GFP 4-22) | CDR3 | Adaptor 2 (GFP 24-42, S, AS) | GFP 4-22 S | GFP 24-42 AS |
| GFP/CDR3.2 | Adaptor 3 (GFP 85-102,S, AS) | CDR3 | Adaptor 4 (GFP 103-120, S, AS) | GFP 85-102 S | GFP 103-120 AS |
| GFP/CDR3.3 | Adaptor 5 (GFP 163-172, S, AS) | CDR3 | Adaptor 6 (GFP 173-184, S, AS) | GFP 163-172 S | GFP 173-184 AS |
| GFP/CDR3.4 | Adaptor 7 (GFP 192-213, S, AS) | CDR3 | Adaptor 8 (GFP 214-235, S, AS) | GFP 192-213 S | GFP 214-235 AS |

BcgI Recognition Site

```
                                      (SEQ ID NO:29)
5'... ˆ10(N) C G A (N)6 T G C (N)12ˆ ... 3'
                                      (SEQ ID NO:30)
3'... ˆ12(N) G C T (N)6 A C G (N)10ˆ ... 5'
```

(3) in each case, one of the BcgI cleavage sites is within the primer (at the 5' end of the primer) and the other is within the amplified V gene, outside of the primer. In the first codon in the case of the 5' primers, and in the last codon in the case of the 3' primers;

(4) the generated overhangs are defined by the known sequences found at these sites; and (5) by annealing to sequences outside the V gene, these primers do not change the sequence of the V gene itself.

V<sub>H</sub> primers

5' primers (SEQ ID NOS:31–54)

1VHL-BcgI-5'  AGG ATC CTC TTY TTG GTG GCC GAA GCC ACT GCW GCC CAC TC

2VHL-BcgI-5'  AGG ATC CTC TTC TTG GTG GCC GAA GCT ACT GCT GCC CAC TC

3VHL-BcgI-5'  AGC ATC CTT TTC TTG GTG GCC GAA CCA ACT GCT GCC CAC TC

4VHL-BcgI-5'  AGG ATC CTC TTC TTG GTG GCC GAA GCT ACT GCC ACC CAC GC

5VHL-BcgI-5'  AGA ATC CTC TTC TTG GTG GCC GAA GCC ACT GCT GCC TAC TC

6VHL-BcgI-5'  AGG GTC TTC TGC TTG CTG GCC GAA GCT CCT GCT GCT CAC TC

7VHL-BcgI-5'  AGG ATC CTC TTC TTG GTG GGC GAA GCG ACT GCT GCC CAC TC

8VHL-BcgI-5'  TCC ACG CTC CTG CTG CTG ACC GAC CCT TCT GCG GTC TTG TC

9VHL-BcgI-5'  TAC ACA CTC CTG CTG CTG ACC GAC CCT TCT GCG GTC TTG TC

10VHL-BcgI-5' HGC TGG GTT TTC CTT GTT GCC GAT TTA RAT GCT GTC CAG TG

11VHL-BcgI-5' AGC TGG GTT TTC CTT GTT GCC GAT WTA AAT GCT GTC CAR TG

12VHL-BcgI-5' AGC TGG ATT TTC CTT GCT GCC GAT TTA AAT GCT GTC CAG TG

13VHL-BcgI-5' AGC TGG ATT TTC CTT TTG GCC GAT TTA AAT GCT GTC CAG TG

14VHL-BcgI-5' AGC TGG CTT TTT CTT GTG GCC GAT TTA AAT GCT GTC CAG TG

15VHL-BcgI-5' AGC TGG GTT TTC CTT GTT GCC GAT TTT AAT GCT GTC CAG TG

16VHL-BcgI-5' AGC TGG GTT TTC CTC GTT GCC GAT TTA AGT GCT GTC CAG TG

17VHL-BcgI-5' AGC TGG GTT TTC CTT GTT GCC GAA TTA GAT GCT GTC CAG TG

18VHL-BcgI-5' AGC TGG GTT TTC CTT GTT GTC GAT TTA CAT GCT GTC CAG TG

19VHL-BcgI-5' TTY TTC CTC CTG CTG GTG GCC GAT CCC AGT GCG GTC CTG YC

20VHL-BcgI-5' TTC TTC CTY CTC CTG GTG GCC GAT CCC AGT GCG GTC CTG TC

21VHL-BcgI-5' ATC CTC GCC CTC CTC CTG GCC GAT CTC CAT GCA GTC TGT TC

22VHL-BcgI-5' ATC CTT GGC CTC CTC CTG GCC GAT CTC CAT GCA GTC TGT GC

23VHL-BcgI-5' ATC TTC CTG CCC GTG CTG GGC GAC CCA TGT GCT GTC CTG TC

24VHL-BcgI-5' AGG ATC CTC TTC TTG GTG GCC GAA GCA ACT GCT GCC CAC TC

3' primers-annealing to 5' end of CH1 of IgG or IgM

IgG primers, sense (SEQ ID NOS:55 and 56)
CC TCC ACC ACG AGC CCA TTG CTC TTC CCC CTG GCA CCC TCC

CY TCC ACC ACG AGC CCA TTG CTC TTC CCC CTG GCG CCC TGC

IgM primers, sense (SEQ ID NO:57)
GG AGT GCA TCG ACC CCA ATG CTT TTC CCC CTC GTC TCC TGT IgG primers, anti-sense (i.e. primers to use) (SEQ ID NOS:58 and 59)
1IgG-BcgI-3'  GGA GGG TGC CAC GGG GAA GAG CAA TGG GCT CGT GGT GGA GG 2IgG-BcgI-3'  GCA GGG CGC CAG GGG GAA GAG CAA TGG GCT CGT GGT GGA RG -continued IgM primers, anti-sense (i.e. primers to use) (SEQ ID NO:60)
1IgM-BcgI-3' ACA GGA GAC GAG GGG GAA AAG CAT TGG GGT CGA TGC ACT CC cDNA from lymphocytes made by hexamer priming is used as a template for the following PCR reactions:

1-24VHL-BcgI-5' and either 1-2IgG-BcgI-3' or 1IgM-BcgI-3'

Conditions for PCR are similar to those described in example 1. PCR will yield a library of fragments of about 410 bp (330 bp VH, plus 41 bp primer sequence at either end). This will give a PCR product with the following structure (using 1VHL-BcgI-5' and 1IgM-BcgI-3'):

5' end amplified $V_H$ gene (SEQ ID NO:61)
AGG ATC CT C T^TY TTG GTG GCC GAA GCC ACT GCW GCC CAC TCC GA^N NNN . . . VH . . .
TCC TAG GA^G A AR AAC CAC CGG CTT CGG TGA CGW CGG GTG AGG^CT N NNN . . . VH . . .

3' end amplified $V_H$ gene (SEQ ID NO:62)
VH . . . NNN T CA^GGG AGT GCA TCG ACC CCA ATG CTT TTC CCC CT C G^TC TCC TGT
VH . . . NNN A^GT CCC TCA CGT AGC TGG GGT TAC GAA AAG GGG GA^G C AG AGG ACA The primer sequences are underlined, the BcgI sites are in bold and the cleavage sites are indicated by "^". Cleavage of this with BcgI (New England Biolabs) (buffer as supplied by NEB: 100 mM NaCl, 10 mM Tris-HCl pH 8.4 25° C., 1 mM DTT, 20 μM S-adenosylmethionine) at 37° C. overnight, will remove 42 bp from each end of the amplified $V_H$ gene, yielding a $V_H$ gene without any additional primers sequences of approximately 330 bp. This can be easily gel purified from either undigested or singly digested PCR product. The structure of such amplified and BcgI cleaved DNA is as follows:

```
  N NNN . . . VH . . . NNN TCA
CTN NNN . . . VH . . . NNN A
```

-continued
```
  N NNN . . . VH . . . NNN TCA
GTN NNN . . . VH . . . NNN A
```

This amplified and BcgI cleaved DNA is available for cloning into any vector, or for use in ribosome or puromycin display by ligation of suitable adaptors and subsequent amplification using suitable primers. The sequences of the adaptors used for cloning into the phagemid display vector, pDAN5, are provided as an example. One of skill in the art will understand that different adaptors will be appropriate for different vectors or purposes. The adaptors are created by purchasing the individual primers, mixing them in equimolar quantities in a buffer comprising 10 mM MgCl$_2$, 50 mM NaCl, 10 mM Tris-HCl, pH 7.9, bringing the temperature to 97° C., and annealing the primers together by cooling to room temperature over 20–30 minutes.

5' end:

CG AAG TTA TCC TCG AGC GGT ACC GA-P    (SEQ ID NO:63)
ATA TGC TTC AAT AGG AGC TCG CCA TGG        (SEQ ID NO:64)

CG AAG TTA TCC TCG AGC GGT ACC CA-P    (SEQ ID NO:65)
ATA TGC TTC PAT AGG AGC TCG CCA TGG        (SEQ ID NO:64)

3' end

GCT AGC GGC AAA CCA ATC CCA AAC CCAC    (SEQ ID NO:67)
p-GT CGA TCG CCG TTT GGT TAG GGT TTG G    (SEQ ID NO:68)

"P" indicates that the primers are phosphorylated at the 5' end. Because of the complementarity between the ends of some of the PCR products after cleavage, the adaptor ligation is done in two steps. First, the 3' adaptor is ligated to the cleaved DNA at a 20:1 molar ratio as described in Sambrook et al., supra, using 1 μg cleaved DNA and 1 μg adaptor. Unligated adaptors are removed using the Qiagen PCR purification kit, which removes DNA fragments less than 100 bp in length. Next the 5' adaptors are ligated using a similar adaptor: cleaved DNA ratio of 20:1. After removal of the unligated 5' adaptors, the structure is as follows:

```
     CG AAG TTA TCC TCG AGC GGT ACC CAN NNN . . . VH . . . NNN TCA GCT AGC GGC AAA CCA ATC CCA AAC CCAC
ATA TGC TTC AAT AGG AGC TCG CCA TGG GTN NNN . . . VH . . . NNN AGT CGA TCG CCG TTT GGT TAG GGT TTG G
(SEQ ID NOS:69-72)
```

Or

```
     CG AAG TTA TCC TCG AGC GGT ACC GAN NNN . . . VH . . . NNN TCA GCT AGC GGC AAA CCA ATC CCA AAC CCAC
ATA TGC TTC AAT AGG AGC TCG CCA TGG CTN NNN . . . VH . . . NNN AGT CGA TCG CCG TTT GGT TAG GGT TTG G
(SEQ ID NOS:73, 70, 74 and 71)
```

There may be some contamination with V$_H$ genes which have become dimerized by virtue of ligation of the 5'GT with the 3'CA. If this is a problem, the correct fragment of approximately 375 bp can be gel purified from the dimerized fragment (about 660 bp).

If there is sufficient DNA, it can be cleaved directly with XhoL and NheI and cloned into pDAN5 cut with the same enzymes. Alternatively, in order to increase the amount of DNA available, the VH gene with ligated adaptors can be reamplified using:

```
5' VH linker TAC TAT ACG AAG TTA TC  (SEQ ID NO:75)

3' VH linker GTG GTT TGG GAT TGG TT  (SEQ ID NO:76)
``` and then cleaved with XhoI (C^TCGAG) and NheI (G^CTAGC). The amplified VH can then be cloned into pDAN5 cleaved with the same enzymes (see later):

```
     TCG AGC GGT ACC SAN NNN . . . VH . . . NNN TCA G       (SEQ ID NO:77)
         CG CCA TGG STN NNN . . . VH . . . NNN AGT CGA TC   (SEQ ID NOS:78 and 79)
     XhoI                                          NheI
```

Example 3

Creation of an Unmodified VK Gene Library

This example demonstrates the generation of V$_\kappa$ sequences for a library. The protocols described above are used. The following primers for the VK gene amplification step:

```
VK 5' primers (SEQ ID NOS:80-94)

1VKL-BcgI-5'  CTC CTG GGG CTC CTG CTA CTC GAG CTC CGT GCT GCC AGA TG

2VKL-BcgI-5'  CTC CTG GGG CTC CTG CWG CTC GAG CTC YCT GCT GCC AGA TG

3VKL-BcgI-5'  CTC CTG GGA CTC CTG CTG CTC GAG CTC CCT GCT ACC AGA TG

4VKL-BcgI-5'  CTC CTG GGG CTC CTG CTG CTC GAG TTC CCT GCT KCC AGR TG

5VKL-BcgI-5'  CKC CTG GGG CTC CTG CTG CTC GAK TTC CCT GCT GCC AGA TG

6VKL-BcgI-5'  CTC CTG GGG CTY CTG CTG CTC GAG CTC CCT GCT GCC ARA TG

7VKL-BcgI-5'  CTC CTG GGG CTG CTA ATG CTC GAG GTC CCT GCA TCC AGT GR

8VKL-BcgI-5'  CTC CTG GGG CTG CTA ATG CTC GAG ATM CCT GCA TCC AGT GC

9VKL-BcgI-5'  CTY CTG GGG CTG CTA ATG CTC GAG GTC YCT GCA TCC AGT GG

10VKL-BcgI-5' CTT CTC TTC CTC CTG CTA CTC GAG CTC MCT GCT ACC ACY GG

11VKL-BcgI-5' TTC TTC TTC CTC CTG CTA CTC GAG CTC CCT GCT ACC ACC GG

12VKL-BcgI-5' GTC TTC ATT TCT CTG TTG CTC GAG ATC TCT GCT GCC TAC GG

13VKL-BcgI-5' CTC CTC AGC TTC CTC CTC CTC GAG ATC TCT GCT ACC AGG GC

14VKL-BcgI-5' CTC ATT GGG TTT CTG CTG CTC GAG GTT CCT GCC TCC AGG GG

15VKL-BcgI-5' TTC CTG CGG CTT CTG CTC CTC GAG GTT CCT GCC TCC AGG GG
```

3' primer—annealing to 5' end of CK

CK primer, sense (SEQ ID NO:95) GA ACT GTG GCG ACA CCA TTG CTC TTC ATC TTC CCG CCA TCT CK primer, anti-sense (i.e. primer to use) (SEQ ID NO:96) 1CK-BcgI-3' AGA TGG CGG GAA GAT GAA GAG CAA TGG TGT CGC CAC AGT TC After amplification, the PCR products are cut with BcgI and gel purified (the correct cleaved fragment will be about 300 bp, compared to 380 for the uncleaved PCR product). The structure of the amplified BcgI cleaved products are as follows:

```
    N NNN . . . VK . . . NNN AAA
  CTN NNN . . . VK . . . NNN T

N NNN . . . VK . . . NNN AAA
  TTN NNN . . . VK . . . NNN T

N NNN . . . VK . . . NNN AAA
  CGN NNN . . . VK . . . NNN T

N NNN . . . VK . . . NNN AAA
  CAN NNN . . . VK . . . NNN T
```

These amplified BcgI cleaved products are available for cloning into any vector, or for use in ribosome or puromycin display by ligation of suitable adaptors and subsequent amplification using suitable primers. As an example, the adaptors used for cloning into pDAN5, our phagemid display vector, will be given. It is clear that the use of different adaptors will be appropriate for different vectors or purposes. The adaptors are created by purchasing the individual primers, mixing them in equimolar quantities in a buffer comprising 10 mM MgCl$_2$, 50 mM NaCl, 10 mM Tris-HCl, pH 7.9, bringing the temperature to 97° C. and annealing them together by cooling to room temperature over 20–30 minutes.

The amplified and digested fragment can be purified by gel purification, or, if the primers are biotinylated at their 5' ends, by removing the biotinylated digested fragments using streptavidin magnetic beads. To clone into pDAN5, the following adaptor primers can be ligated:

5' end

```
    GCA GCA AGC GGC GCG CAT GCC GA-P      (SEQ ID NO:97)
GAG CGT CGT TCG CCG CGC GTA CGG          (SEQ ID NO:98)

GCA GCA AGC GGC GCG CAT GCC AA-P      (SEQ ID NO:99)
GAG CGT CGT TCG CCG CGC GTA CGG          (SEQ ID NO:98)

GCA GCA AGC GGC GCG CAT GCC GC-P      (SEQ ID NO:100)
GAG CGT CGT TCG CCG CGC GTA CGG          (SEQ ID NO:98)

GCA GCA AGC GGC GCG CAT GCC GT-P      (SEQ ID NO:101)
GAG CGT CGT TCG CCG CGC GTA CGG          (SEQ ID NO:98)
```

3' end

```
    TCC GGA GGG TCG ACC ATA ACT TCG TA    (SEQ ID NO:102)
P-TT AGG CCT CCC AGC TGG TAT TGA         (SEQ ID NO:103)
```

"P" indicates that the primers are phosphorylated at the 5' end. Because there is complementarity between the ends of some of the PCR products after ligation, the adaptor ligation is done in two steps. First, the 3' adaptor is ligated to the cleaved DNA at a 20:1 molar ratio (this protocol is described in detail in Molecular Cloning, 3$^{rd}$ Edition, Sambrook & Russell, p 1.88) using 1 µg cleaved DNA and 1 µg adaptor. Unligated adaptors are removed using the Qiagen PCR purification kit, which removes DNA fragments less than 100 bp in length. Next the 5' adaptors are ligated using a similar adaptor: cleaved DNA ratio of 20:1. After removal of the unligated 5' adaptors, the structure is as follows:

```
    GCA GCA AGC GGC GCG CAT GCC GAN NNN . . . VK . . . NNN AAA TCC GGA GGG TCG ACC ATA ACT TCG TA
GAG CGT CGT TCG CCG CGC GTA CGG CTN NNN . . . VK . . . NNN TTT AGG CCT CCC AGC TGG TAT TGA
(SEQ ID NOS:104-109)

GCA GCA AGC GGC GCG CAT GCC AAN NNN . . . VK . . . NNN AAA TCC GGA GGG TCG ACC ATA ACT TCG TA
GAG CGT CGT TCG CCG CGC GTA CGG TTN NNN . . . VK . . . NNN TTT AGG CCT CCC AGC TGG TAT TGA
(SEQ ID NOS:108, 105, 109 and 107)

GCA GCA AGC GGC GCG CAT GCC GCN NNN . . . VK . . . NNN AAA TCC GGA GGG TCG ACC ATA ACT TCG TA
GAG CGT CGT TCG CCG CGC GTA CGG CGN NNN . . . VK . . . NNN TTT AGG CCT CCC AGC TGG TAT TGA
(SEQ ID NOS:110, 105, 111 and 107)

GCA GCA AGC GGC GCG CAT GCC GTN NNN . . . VK . . . NNN AAA TCC GGA GGG TCG ACC ATA ACT TCG TA
GAG CGT CGT TCG CCG CGC GTA CGG CAN NNN . . . VK . . . NNN TTT AGG CCT CCC AGC TGG TAT TGA
(SEQ ID NOS:112, 105, 113 and 107)
```

There may be some contamination with VK genes which have become dimerized by virtue of ligation of the 5'TT with the 3'AA, and 5' CG with itself. If this is a problem, the correct fragment of approximately 375 bp can be gel purified from dimerized (or larger) fragments (660 bp and above).

If there is sufficient DNA, this can be cleaved directly with BssHII and SalI and cloned into pDAN5 cut with the same enzymes. In order to increase the amount of DNA available, the VL gene with ligated adaptors can be reamplified using:

```
                                                        (SEQ ID NO:114)
5' VL linker GCA GCA AGC GGC GCG CA (SEQ ID NO:115)
3' VL linker CGA AGT TAT GGT CGA CCC TC
``` and then cleaved with BssHII (G^CGCGC) and SalI (G^TCGAC). The amplified VK can then be cloned into pDAN5 cleaved with the same enzymes.

```
C GCG CAT GCC GAN NNN . . . VK . . . NNN AAA TCC GGA GGG
      GTA CGG CTN NNN . . . VK . . . NNN TTT AGG CCT CCC AGC T
(SEQ ID NOS:116-119)

C GCG CAT GCC AAN NNN . . . VK . . . NNN AAA TCC GGA GGG
      GTA CGG TTN NNN . . . VK . . . NNN TTT AGG CCT CCC AGC T
(SEQ ID NOS:120, 117, 121 and 119)

C GCG CAT GCC GCN NNN . . . VK . . . NNN AAA TCC GGA GGG
      GTA CGG CGN NNN . . . VK . . . NNN TTT AGG CCT CCC AGC T
(SEQ ID NOS:122, 117, 123 and 119)

C GCG CAT GCC GTN NNN . . . VK . . . NNN AAA TCC GGA GGG
      GTA CGG CAN NNN . . . VK . . . NNN TTT AGG CCT CCC AGC T
(SEQ ID NOS:124, 117, 125 and 119)
```

Example 4

Creation of an Unmodified VL Gene Library

This example demonstrates the generation of $V_\lambda$ sequences for a library. The protocol described for the creation of the $V_H$ library is followed, except that the following primers are used for the first amplification:

```
VL 5' primers (SEQ ID NOS:126-147)

1VLL-BcgI-5'  CTC YTC CTC ACC CTC MTC ACC GAC TGT GCT GCG TCC TGG GC

2VLL-BcgI-5'  CTC CTC CTC ACT CTC CTC GCC GAC TGC ACT GCG TCC TGG GC

3VLL-BcgI-5'  CTC CTC CTC ACC CTT CTC ATC GAC TGC ACT GCG TCC TGG GC

4VLL-BcgI-5'  CTC CTC CTC ASC CTC CTC ACC GAG GGC ACT GCR TCC TGG GC

5VLL-BcgI-5'  CTG CTC CTC ACY CTC CTC ACC GAG GRC ACT GCG TCC TGG GC

6VLL-BcgI-5'  CTC TTC CTC GGC GTC CTT GCC GAC TGC ACT GCA TCC GTG GC

7VLL-BcgI-5'  CTC CTT CTG AGC CTC CTT GCC GAC TTT ACT GCT TCT GTG GC

8VLL-BcgI-5'  CTM CTK CTC CCC CTC CTC ACC GAC TGC ACT GCC TCT GAG GC
```

-continued

```
 9VLL-BcgI-5' CTC TGG CTC ACT CTC CTC ACC GAT TGC ATT GCT TCT GTG GT
10VLL-BcgI-5' CTC CTC CTC GGC CTC CTC TCC GAC TGC ACT GCC TCT GTG AC
11VLL-BcgI-5' CTC CTG CTC CCA CTC CTC AAC GAC TAC ACT GCC TCT ATT GC
12VLL-BcgI-5' CTC CTG CTC CCC CTC CTC ATC GAC TGC ACT GCC TCT GTG GC
13VLL-BcgI-5' TTC TAC CTA CTG CCC TTC ATC GAC TCC ACT GCT CTC TGT GC
14VLL-BcgI-5' CTC CTC TTC CCT CTC CTC CTC GAC TGG ACT GCG TCT CTC TC
15VLL-BcgI-5' CTC TTC CTC ACC CTC CTC CTC GAC TGC ACT GCG TCT CTC TC
16VLL-BcgI-5' CTY CTT CTC KTG CTC CTC TCC GAC TGC ACT GCT TCC CTC TC
17VLL-BcgI-5' CTC CTC CTC CTG TTC CTC TCC GAC TGC ACT GCT TCC CTC TC
18VLL-BcgI-5' CTA CTT CTC ACC CTC CTC GCC GAC TGC ACT GCT TCT TGG GC
19VLL-BcgI-5' CTC TTT CTG TTC CTC CTC ACC GAC TGC CCT GCG TCC AAT TC
20VLL-BcgI-5' CTT CTC CTC GGA CTC CTT GCC GAT GGA TCT GCA GTG GAT TC
21VLL-BcgI-5' CTG CTC CTC ACC CTC CTC AGC GAC CTC ACT GCG TCC CTC TC
22VLL-BcgI-5' CTC CTC CTG ACC CTC CTC ACC GAC TCT GCT GCG TCA GTG GT
```

3' primers - annealing to 5' end of CL

CL primer, sense (SEQ ID NOS:148 and 149)
```
GT CAG CCC ACG ACC AAC CTG CCG GTC ACT CTG TTC CCG CCC

GT CAG CCC ACG ACT GCC CTG CCG GTC ACT CTG TTC CCR CCC
```

CL primer, anti-sense (i.e. primer to use) (SEQ ID NOS:150 and 151)
```
1CL-BcgI-3' GGG CGG GAA CAG AGT GAC CGG CAG GTT GGT CGT GGG CTG AC 2CL-BcgI-3' GGG YGG GAA CAG AGT GAC CGG CAG GGC AGT CGT GGG CTG AC
```

3' primers—annealing to 5' end of CL

After amplification, the PCR products are cut with BcgI and gel purified (the correct cleaved fragment will be about 300 bp, compared to 380 for the uncleaved PCR product). The structure of the amplified BcgI cleaved products are as follows:

```
  N NNN . . . Vλ . . . NNN CTA
GTN NNN . . . Vλ . . . NNN G

N NNN . . . Vλ . . . NNN CTA
AGN NNN . . . Vλ . . . NNN G

N NNN . . . Vλ . . . NNN CTA
GAN NNN . . . Vλ . . . NNN G

N NNN . . . Vλ . . . NNN CTA
TTN NNN . . . Vλ . . . NNN G

N NNN . . . Vλ . . . NNN CTC
GTN NNN . . . Vλ . . . NNN G
```

-continued
```
  N NNN . . . Vλ . . . NNN CTC
AGN NNN . . . Vλ . . . NNN G

N NNN . . . Vλ . . . NNN CTC
GAN NNN . . . Vλ . . . NNN G

N NNN . . . Vλ . . . NNN CTC
TTN NNN . . . Vλ . . . NNN G
```

This is available for cloning into any vector, or for use in ribosome or puromycin display by ligation of suitable adaptors and subsequent amplification using suitable primers. As an example, the adaptors used for cloning into pDAN5, our phagemid display vector, will be given. It is clear that the use of different adaptors will be appropriate for different vectors or purposes. The adaptors are created by purchasing the individual primers, mixing them in equimolar quantities in a 10 mM MgCl2, 50 mM NaCl, 10 mM Tris-HCl, pH7.9 buffer, bringing the temperature to 97° C. and annealing them together by cooling to room temperature over 20–30 minutes. This can be done in a PCR machine with a suitable program.

5' end:
```
    GCA GCA AGC GGC GCG CAT GCC CA-P        (SEQ ID NO:152)

GAG CGT CGT TCG CCG CGC GTA CGG         (SEQ ID NO:153)
```

```
    GCA GCA AGC GGC GCG CAT GCC TC-P      (SEQ ID NO:154)

GAG CGT CGT TCG CCG CGC GTA CGG           (SEQ ID NO:153)

GCA GCA AGC GGC GCG CAT GCC CT-P      (SEQ ID NO:155)

GAG CGT CGT TCG CCG CGC GTA CGG           (SEQ ID NO:153)

GCA GCA AGC GGC GCG CAT GCC AA-P      (SEQ ID NO:156)

GAG CGT CGT TCG CCG CGC GTA CGG           (SEQ ID NO:153)

3' end:

TCC GGA GGG TCG ACC ATA ACT TCG TA    (SEQ ID NO:157)

P-AG AGG CCT CCC AGC TGG TAT TGA          (SEQ ID NO:158)

TCC GGA GGG TCG ACC ATA ACT TCG TA    (SEQ ID NO:157)

P-AT AGG CCT CCC AGC TGG TAT TGA          (SEQ ID NO:159)
```

P indicates that the primers are phosphorylated at the 5' end. Because there is complementarity between the ends of some of the PCR products after ligation, the adaptor ligation is done in two steps. First, the 3' adaptors are ligated to the cleaved DNA at a 20:1 molar ratio (this protocol is described in detail in Molecular Cloning, 3$^{rd}$ Edition, Sambrook & Russell, p 1.88) using 1 μg cleaved DNA and 1 μg adaptor. Unligated adaptors are removed using the Qiagen PCR purification kit, which removes DNA fragments less than 100 bp in length. Next the 5' adaptors are ligated using a similar adaptor: cleaved DNA ratio of 20:1. After removal of the unligated 5' adaptors, the structure is as follows:

```
    GCA GCA AGC GGC GCG CAT GCC CAN NNN . . . Vλ . . . NNN CTA TCC GGA GGG TCG ACC ATA ACT TCG TA
GAG CGT CGT TCG CCG CGC GTA CGG GTN NNN . . . Vλ . . . NNN GAT AGG CCT CCC AGC TGG TAT TGA
(SEQ ID NOS:160-163)

GCA GCA AGC GCC GCG CAT GCC TCN NNN . . . Vλ . . . NNN CTA TCC GGA GGG TCG ACC ATA ACT TCG TA
GAG CGT CGT TCG CCG CGC GTA CGG AGN NNN . . . Vλ . . . NNN GAT AGG CCT 000 AGC TGG TAT TGA
(SEQ ID NOS:164, 161, 165 and 163)

GCA GCA AGC GGC GCG CAT GCC CTN NNN . . . Vλ . . . NNN CTA TCC GGA GGG TCG ACC ATA ACT TCG TA
GAG CGT CGT TCG CCG CGC GTA CGG GAN NNN . . . Vλ . . . NNN GAT AGG CCT CCC AGC TGG TAT TGA
(SEQ ID NOS:166, 161, 167 and 163)

GCA GCA AGC GGC GCG CAT GCC AAN NNN . . . Vλ . . . NNN CTA TCC GGA GGG TCG ACC ATA ACT TCG TA
GAG CGT CGT TCG CCG CGC GTA CGG TTN NNN . . . Vλ . . . NNN GAT AGG CCT CCC AGC TGG TAT TGA
(SEQ ID NOS:168, 161, 169 and 163)

GCA GCA AGC GGC GCG CAT GCC CAN NNN . . . Vλ . . . NNN CTC TCC GGA GGG TCG ACC ATA ACT TCG TA
GAG CGT CGT TCG CCG CGC GTA CGG GTN NNN . . . Vλ . . . NNN GAG AGG CCT CCC AGC TGG TAT TGA
(SEQ ID NOS:160, 170, 162 and 171)

GCA GCA AGC GGC GCG CAT GCC TCN NNN . . . Vλ . . . NNN CTC TCC GGA GGG TCG ACC ATA ACT TCG TA
GAG CGT CGT TCG CCG CGC GTA CGG AGN NNN . . . Vλ . . . NNN GAG AGG CCT CCC AGC TGG TAT TGA
(SEQ ID NOS:164, 170, 165 and 171)

GCA GCA AGC GGC GCG CAT GCC CTN NNN . . . Vλ . . . NNN CTC TCC GGA GGG TCG ACC ATA ACT TCG TA
GAG CGT CGT TCG CCG CGC GTA CGG GAN NNN . . . Vλ . . . NNN GAG AGG CCT CCC AGC TGG TAT TGA
(SEQ ID NOS:166, 170, 165 and 171)

GCA GCA AGC GGC GCG CAT GCC AAN NNN . . . Vλ . . . NNN CTC TCC GGA GGG TCG ACC ATA ACT TCG TA
GAG CGT CGT TCG CCG CGC GTA CGG TTN NNN . . . Vλ . . . NNN GAG AGG CCT CCC AGC TGG TAT TGA
(SEQ ID NOS:168, 170, 169 and 171)
```

There may be some contamination with VL genes which have become dimerized by virtue of ligation of the 5'AG with the 3'TC. If this is a problem, the correct fragment of approximately 375 bp can be gel purified from the dimerized fragment (about 660 bp).

If there is sufficient DNA, this can be cleaved directly with BssHII and SalI and cloned into pDAN5 cut with the same enzymes. In order to increase the amount of DNA available, the VL gene with ligated adaptors can be reamplified using the same primers as before:

```
5' VL linker GCA GCA AGC GGC GCG CA        (SEQ ID NO:114)

3' VL linker CGA AGT TAT GGT CGA CCC TC    (SEQ ID NO:115)
``` and then cleaved with BssHII and SalI. The amplified $V_L$ can then be cloned into pDAN5 cleaved with the same enzymes (see below)

```
C GCG CAT GCC CAN NNN . . . Vλ . . . NNN CTA TCC GGA GGG
      GTA CGG GTN NNN . . . Vλ . . . NNN GAT AGG CCT CCC AGC T
(SEQ ID NOS:172–175)

C GCG CAT GCC TCN NNN . . . Vλ . . . NNN CTA TCC GGA GGG
      GTA CGG AGN NNN . . . Vλ . . . NNN GAT AGG CCT CCC AGC T
(SEQ ID NOS:176, 173, 177 and 175)

C GCG CAT GCC CTN NNN . . . Vλ . . . NNN CTA TCC GGA GGG
      GTA CGG GAN NNN . . . Vλ . . . NNN CAT AGG CCT CCC AGC T
(SEQ ID NOS:178, 173, 179 and 175)

C GCG CAT GCC AAN NNN . . . Vλ . . . NNN CTA TCC GGA GGG
      GTA CGG TTN NNN . . . Vλ . . . NNN CAT AGG CCT CCC AGC T
(SEQ ID NOS:180, 173, 181 and 175)

C GCG CAT GCC CAN NNN . . . Vλ . . . NNN CTC TCC GGA GGG
      GTA CGG GTN NNN . . . Vλ . . . NNN GAG AGG CCT CCC AGC T
(SEQ ID NOS:172, 182, 174 and 183)

C GCG CAT GCC TCN NNN . . . Vλ . . . NNN CTC TCC GGA GGG
      GTA CGG AGN NNN . . . Vλ . . . NNN CAC AGG CCT CCC AGC T
(SEQ ID NOS:176, 182, 177 and 183)

C GCG CAT GCC CTN NNN . . . Vλ . . . NNN CTC TCC GGA GGG
      GTA CGG GAN NNN . . . Vλ . . . NNN CAC AGG CCT CCC AGC T
(SEQ ID NOS:178, 182, 179 and 183)

C GCG CAT GCC AAN NNN . . . Vλ . . . NNN CTC TCC GGA GGG
      GTA CGG TTN NNN . . . Vλ . . . NNN CAC AGG CCT CCC AGC T
(SEQ ID NOS:180, 182, 181 and 183)
```

Example 5

Amplification of Other V Genes

Amplification of other V genes can be carried out using different enzymes. For example, MmeI and Bce83I are two restriction enzymes which are similar to BpmI, in that they cut only once outside their recognition site. MmeI (TCCRAC20/18) and Bce83I (CTTGAG16/14) cut different human V genes. However, they cut sets of V genes in which only 1 V gene (DP78), which represents less than 0.5% of the total, is cut by both. As a result, these two enzymes can be used together to create a complete representation of all human V genes, with the exception of DP78. An examination of the number of times these enzymes cut V, D and J genes, reveals that they cut overlapping sets of these genes, such that only DP78 is cut by both enzymes. This is shown in the table below:

|  | Bce83I CTTGA G16/14 | MmeI TCCRA C20/18 |
|---|---|---|
| VH Genes |  |  |
| >COS-12+ |  |  |
| >DP-10/hv 1051 . . . + | X |  |
| >DP-14/V1-18+ | X |  |
| >DP-15/V1-8+ | X |  |
| >DP-2/V71-5+ | X |  |
| >DP-21/4d275a+ | X |  |
| >DP-25/VI-3b+ | X |  |
| >DP-28/Vh2-MC1 . . . + |  |  |
| >DP-29/12-2+ | X |  |
| >DP-3+ | X |  |
| >DP-31/V3-9P . . . + |  | X |
| >DP-32/V3-20+ |  |  |
| >DP-33/V3-43+ |  |  |
| >DP-35/V3-11 . . . |  |  |
| >DP-38/9-1 . . . + | X |  |
| >DP-4+ | X |  |
| >DP-42+ |  |  |
| >DP-46/3d216 . . . + |  |  |
| >DP-47/V3-23 . . . + |  | X |
| >DP-48/13-2+ |  |  |
| >DP-49/1.9III . . . + |  |  |
| >DP-5/V1-24P+ | X |  |
| >DP-50/hv3019b9 . . . + |  |  |
| >DP-51+ |  |  |
| >DP-53/hvm148 . . . + |  |  |
| >DP-54/V3-7 . . . + |  |  |
| >DP-63/VH4.21 . . . + | X |  |
| >DP-64/3d216d+ | X |  |
| >DP-65/3d75d . . . + | X |  |
| >DP-66/V71-2 . . . + | X |  |

| | Bce83I CTTGA G16/14 | MmeI TCCRA C20/18 |
|---|---|---|
| >DP-67/VH4-4B+ | X | |
| >DP-68/1.9II . . . + | X | |
| >DP-7/21-2 . . . + | X | |
| >DP-70/4d68 . . . + | X | |
| >DP-71/3d197d . . . + | X | |
| >DP-73/V5-51 . . . + | | |
| >DP-74/VH-VI . . . + | X | |
| >DP-75/V1-2 . . . + | X | |
| >DP-77/WHG16+ | | |
| >DP-78/3d230d . . . + | X | X |
| >DP-79/4d154 . . . + | X | |
| >DP-88/hv1051K . . . + | X | |
| >V2-V6/DP-26+ | | |
| >V3-49+ | X | |
| >V3-64/YAC-6+ | | |
| >VH32Sanz+ | | |
| >VII-5+ | | |
| >YAC-5+ | | |
| >YAC-9/COS-27 . . . + | | |
| VK Genes | | |
| >A18B+ | | |
| >A30/SG3+ | | |
| >DPK10/L24a . . . + | | X |
| >DPK12/A2+ | | X |
| >DPK13/O11 . . . + | | X |
| >DPK15/A19 . . . + | | |
| >DPK16/A23+ | X | |
| >DPK18/A17+ | | |
| >DPK19/A1+ | | |
| >DPK2/L14+ | | |
| >DPK20/A11 . . . + | | |
| >KPK21/humkv328h5+ | | |
| >DPK22/A27 . . . + | | |
| >DPK23/L25 . . . + | | |
| >DPK24/VkIVKlobeck..+ | | X |
| >DPK25/A14+ | | |
| >DPK26/A26 . . . + | | |
| >DPK3/L11+ | | |
| >DPK4/A20+ | | |
| >DPK5/Vb+ | | |
| >DPK6/Vb"+ | | |
| >DPK7/HK134 . . . + | | |
| >DPK8/Vd+ | | |
| >DPK9/O12 . . . + | | |
| >EV15+ | | |
| >HK102/V1+ | | |
| >HK137+ | | |
| >L16/humkv3les . . . + | | |
| >L23/L23a+ | | |
| >Va'+ | | |
| >copy Va'+ | | |
| >Ve+ | | |
| >Vg"/13K11 . . . + | | X |
| >Vg/38K . . . + | | X |
| VL Genes | | |
| >DPL16/VL3.1 . . . + | | |
| >10a.872F9+ | X | |
| >1a.11.2/DPL1 . . . + | | X |
| >1b.366F5/DPL5 . . . + | | X |
| >1c.10.2/DPL2 . . . + | | X |
| >1e.10.2/DPL8 . . . + | | X |
| >1g.400B5/DPL3 . . . + | | X |
| >2a2.272A12/DPL11 . . . + | | |
| >2b2.400B5+ | | |
| >2c118D9/V1-2+ | | |
| >2d.9D11/DPL13 . . . + | | |
| >2e2.2/V1-3+ | | |
| >3a.119B4/V2-11+ | | |
| >3e.272A12/V2-15+ | | |
| >3j.118D9/V2-6+ | | X |
| >3m.102D1+ | | |
| >3p.81A4/V2-7+ | | |
| >3R.9c5/DPL23 . . . + | | X |
| >4a.366F5+ | | X |
| >4b.68B6/V5-6 . . . + | | |
| >4c.127E5/DPL24 . . . + | | X |
| >5b.366F5/V4-4+ | | X |
| >5c366F5+ | | |
| >5e.366F5/V40-1+ | | |
| >6a.366F5/V1-22 . . . + | | X |
| >7A.2.3/DPL18 . . . + | | |
| >7b.400B5/DPL19+ | | |
| >8a88E1/DPL21 . . . + | X | |
| >9a.366F5/DPL22 . . . + | | |
| >IGLV3S2+ | | X |
| >V2-19 | | |
| D Genes | | |
| >D1 | | |
| >D1-1 | | |
| >D1-14/DM2 | | |
| >D1-20 | | |
| >D1-26 | | |
| >D1-7/DM1 | | |
| >D2-15/D2 | | |
| >D2-2 | | |
| >D2-21 | | |
| >D2-8/DLR1 | | |
| >D3 | | |
| >D3-10/DXP'1 | | |
| >D3-16 | | |
| >D3-22/D21-9 | | |
| >D3-3/DXP4 | | |
| >D3-9/DXP1 . . . | | |
| >D4 | | |
| >D4-11/DA1 | | |
| >D4-17 | | |
| >D4-23 | | |
| >D4-4/DA4 | | |
| >D4-b | | |
| >D5-12/DK1 | | |
| >D5-18 | | |
| >D5-24 | | |
| >D5-5/DK4 | | |
| >D6-13/DN1 | | |
| >D6-19 | | |
| >D6-25 | | |
| >D6-6/DN4 | | |
| >D7-27/DHQ52 | | |
| JH Genes | | |
| >JH1 | | |
| >JH2 | | |
| >JH3a | | |
| >JH3b | | |
| >JH4a | | |
| >JH4b | | |
| >JH4d | | |
| >JH5a | | |
| >JH5b | | |
| >JH6a | | |
| >JH6b | | |
| >JH6c | | |
| JK Genes | | |
| >JK1 | | |
| >JK2 | | |
| >JK3 | | |
| >JK4 | | |
| >JK5 | | |
| JL Genes | | |
| >JL1 | | |
| >JL2/JL3a | | |
| >JL3b | | |
| >JL4 | | |
| >JL5 | | |
| >JL6a | | |

| | Bce83I<br>CTTGA<br>G16/14 | MmeI<br>TCCRA<br>C20/18 |
|---|---|---|
| >JL6b<br>>JL7 | | |

To create primers which would be used with these enzymes, the following steps would be taken:
1) align all the V$_H$ gene leader sequences (see VBASE sopra);
2) substitute bases −15 to −20 with the Bce83I restriction enzyme site (CTTGAG);
3) remove those V$_H$ genes which are cut with Bce83I by reference to the table above;
4) remove all bases from the beginning of the leader to position −29;
5) remove the base at −1
6) remove all those sequences which are now identical; and
7) the primers which remain can now be used to amplify the 5' end of a subset of V$_H$ genes.

For the remaining V$_H$ genes, which are cut by Bce83I, the enzyme MmeI is to be used in the following way:
1) align all the VH gene leader sequences (see VBASE sopra);
2) substitute bases −19 to −24 with the MmeI restriction enzyme site (TCCAAC);
3) remove those VH genes which are cut with MmeI by reference to the table above;
4) remove all bases from the beginning of the leader to position −33;
5) remove the base at −1;
6) remove all those sequences which are now identical; and
7) the primers which remain can now be used to amplify the 5' end of a subset of VH genes. The sum of the genes amplified by these two primer sets will constitute almost the whole VH gene repertoire. A similar procedure is taken for the VL and VK genes.

The 3' primer for each set is identified similarly, except that the Bce83I site is positioned at positions +15 to +20 in the constant region sequence (CH1 or IgG or IgM; CK or CL), and the MmeI site is positioned at position +19 to +24. The base at position +1 is removed, and for Bce83I, the bases to +29 are retained beyond the Bce83I sequence, and for MmeI, the bases to +33 are retained beyond the MmeI sequence. The primers so identified, are then reversed and complemented to be used with the appropriate 5' primers. After amplification and digestion with the appropriate enzyme (Bce83I or MmeI) the cut fragments can be gel purified and ligated to the adaptors described above (BcgI).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preparing an amplified product that is free of amplification primer sequences, said method comprising:
   (a) amplifying a target nucleic acid sequence encoding an antibody variable region or fragment of said variable region in an amplification reaction comprising:
      (i) a first primer that specifically anneals to a region upstream of a target polynucleotide sequence, wherein the first primer comprises a first restriction enzyme recognition site that is recognized by a first restriction enzyme that cleaves at a distance from the recognition site; and
      (ii) a second primer that specifically anneals to a region downstream of the target polynucleotide sequence, wherein the second primer comprises a second restriction enzyme recognition site that is recognized by a second restriction enzyme that cleaves at a distance from the recognition site; and
   (b) cleaving said amplified product with the first and second restriction enzymes, thereby obtaining the amplified product that is free of amplification primer sequences.

2. The method of claim 1, wherein at least one restriction enzyme cleaves at two sites at a distance from its recognition site.

3. The method of claim 1, wherein at least one restriction enzyme recognition site is a non-palindromic sequence.

4. The method of claim 1, wherein at least one restriction enzyme recognition site is a palindromic sequence.

5. The method of claim 1, wherein at least one restriction enzyme recognition site is an interrupted sequence.

6. The method of claim 1, wherein at least one restriction enzyme cleaves at a position at least 6 base pairs downstream of its recognition site.

7. The method of claim 1, wherein the first and second restriction enzyme recognition sites are the same.

8. The method of claim 1, wherein at least one of the restriction enzymes is a member selected from the group consisting of BpmI, EcoP15I, Bce83I, BsgI, Eco57I, GsuI, and MmeI.

9. The method of claim 8, wherein the restriction enzyme is BpmI.

10. The method of claim 1, wherein at least one of the restriction enzymes is a member selected from the group consisting of AloI, BaeI, BcgI, BplI, BsaXI, Bsp24I, CjeI, FalI, PpiI, and PsrI.

11. The method of claim 1, wherein the target nucleic acid sequence comprises an antibody variable region.

12. The method of claim 11, wherein the restriction enzyme is BcgI.

13. The method of claim 11, wherein the restriction enzyme is a member selected from the group consisting of MmeI or Bce83I.

14. The method of claim 1, wherein the target nucleic acid sequence comprises an antibody hypervariable region.

15. The method of claim 14, further wherein the first and second primers specifically hybridize to the region encoding an antibody framework region.

16. A method of preparing a library, said method comprising the steps of:
 (a) preparing an amplified product that is free of amplification primer sequences by amplifying a target nucleic acid sequence encoding an antibody variable region or fragment of said variable region in an amplification reaction comprising:
  (i) a first primer that specifically anneals to a region upstream of a target polynucleotide sequence, wherein the first primer comprises a first restriction enzyme recognition site that is recognized by a first restriction enzyme that cleaves at a distance from the recognition site; and
  (ii) a second primer that specifically anneals to a region downstream of the target polynucleotide sequence, wherein the second primer comprises a second restriction enzyme recognition site that is recognized by a second restriction enzyme that cleaves at a distance from the recognition site;
 (b) cleaving said amplified product with the first and second restriction enzymes, thereby obtaining the amplified product that is free of amplification primer sequences; and
 (c) linking said amplified product to a library vehicle.

17. The method of claim 16, wherein the library vehicle comprises a cloning vector.

18. The method of claim 17, wherein the library vehicle comprises a phage display vector.

19. The method of claim 17, wherein the library vector comprises a bacterial vector.

20. The method of claim 17, wherein the library vehicle comprises a yeast vector.

21. The method of claim 16, wherein the library vehicle comprises a nucleic acid encoding a enzyme.

22. The method of claim 16, wherein the library vehicle comprises a nucleic acid encoding a heterologous protein.

23. The method of claim 16, wherein the library vehicle comprises a nucleic acid encoding a GFP scaffold.

24. The method of claim 16, wherein the library vehicle comprises a nucleic acid encoding a coat protein.

25. The method of claim 16, wherein the library vehicle comprises an oligonucleotide joined to puromycin.

26. The method of claim 16, wherein the library vehicle comprises a ribosome.

27. The method of claim 16, wherein the step of linking the amplified product comprises ligating an adaptor oligonucleotide to the amplified product, thereby forming a linked amplified product; and amplifying the linked ligated product.

28. The method of claim 16, wherein at least one restriction enzyme cleaves at two sites at a distance from its recognition site.

29. The method of claim 16, wherein at least one restriction enzyme recognition site is a non-palindromic sequence.

30. The method of claim 16, wherein at least one restriction enzyme recognition site is a palindromic sequence.

31. The method of claim 16, wherein at least one restriction enzyme recognition site is an interrupted sequence.

32. The method of claim 16, wherein at least one restriction enzyme cleaves at a position at least 9 base pairs downstream of its recognition site.

33. The method of claim 16, wherein the first and second restriction enzyme recognition sites are the same.

34. The method of claim 16, wherein at least one of the restriction enzymes is a member selected from the group consisting of BpmI, EcoP15I, Bce83I, BsgI, Eco57I, GsuI, and MmeI.

35. The method of claim 16, wherein the restriction enzyme is BpmI.

36. The method of claim 16, wherein at least one of the restriction enzymes is a member selected from the group consisting of AloI, BaeI, BcgI, BplI, BsaXI, Bsp24I, CjeI, FalI, PpiI, and PsrI.

37. The method of claim 16, wherein the restriction enzyme is BcgI.

38. The method of claim 16, wherein the restriction enyzme is a member selected from the group consisting of MmeI and Bce83I.

39. The method of claim 16, wherein the target nucleic acid sequence comprises an antibody variable region.

40. The method of claim 39, wherein the first and second primers specifically hybridize to the region flanking the antibody variable region.

41. The method of claim 16, wherein the target nucleic acid sequence comprises an antibody hypervariable region.

42. The method of claim 16, wherein the first and second primers specifically hybridize to the region encoding an antibody framework region.

43. The method of claim 42, further wherein the region flanking the target nucleic acid sequence is an antibody framework region.

* * * * *

SEQUENCE LISTING

```
<160> NUMBER OF SEQ ID NOS: 183

<210> SEQ ID NO 1
<211> LENGTH: 27
<212> TYPE: DNA
<213> ORGANISM: Artificial Sequence
<220> FEATURE:
<223> OTHER INFORMATION: VR35-1 primer
<220> FEATURE:
<221> NAME/KEY: modified_base
<222> LOCATION: (1)...(1)
<223> OTHER INFORMATION: n = c conjugated to biotin

<400> SEQUENCE: 1
ngtgctggag tattactgtg cragaga                                      27

<210> SEQ ID NO 2
<211> LENGTH: 27
<212> TYPE: DNA
<213> ORGANISM: Artificial Sequence
<220> FEATURE:
<223> OTHER INFORMATION: VR35-2 primer
<220> FEATURE:
<221> NAME/KEY: modified_base
<222> LOCATION: (1)...(1)
<223> OTHER INFORMATION: n = c conjugated to biotin

<400> SEQUENCE: 2
ngtgctggag tattactatg cgagaga                                      27
```

-continued

```
<210> SEQ ID NO 3
<211> LENGTH: 27
<212> TYPE: DNA
<213> ORGANISM: Artificial Sequence
<220> FEATURE:
<223> OTHER INFORMATION: VR35-3 primer
<220> FEATURE:
<221> NAME/KEY: modified_base
<222> LOCATION: (1)...(1)
<223> OTHER INFORMATION: n = c conjugated to biotin

<400> SEQUENCE: 3
ngtgctggag tattactgtg crrcaga                                              27

<210> SEQ ID NO 4
<211> LENGTH: 27
<212> TYPE: DNA
<213> ORGANISM: Artificial Sequence
<220> FEATURE:
<223> OTHER INFORMATION: VR35-4 primer
<220> FEATURE:
<221> NAME/KEY: modified_base
<222> LOCATION: (1)...(1)
<223> OTHER INFORMATION: n = c conjugated to biotin

<400> SEQUENCE: 4
ngtgctggag tattactgta ccacaga                                              27

<210> SEQ ID NO 5
<211> LENGTH: 27
<212> TYPE: DNA
<213> ORGANISM: Artificial Sequence
<220> FEATURE:
<223> OTHER INFORMATION: VR35-5 primer
<220> FEATURE:
<221> NAME/KEY: modified_base
<222> LOCATION: (1)...(1)
<223> OTHER INFORMATION: n = c conjugated to biotin

<400> SEQUENCE: 5
ngtgctggag tattactgtr cyagaga                                              27

<210> SEQ ID NO 6
<211> LENGTH: 27
<212> TYPE: DNA
<213> ORGANISM: Artificial Sequence
<220> FEATURE:
<223> OTHER INFORMATION: VR35-6 primer
<220> FEATURE:
<221> NAME/KEY: modified_base
<222> LOCATION: (1)...(1)
<223> OTHER INFORMATION: n = t conjugated to biotin

<400> SEQUENCE: 6
nktgctggag tattactgtg craaaga                                              27

<210> SEQ ID NO 7
<211> LENGTH: 27
<212> TYPE: DNA
<213> ORGANISM: Artificial Sequence
<220> FEATURE:
<223> OTHER INFORMATION: VR35-7 primer
<220> FEATURE:
<221> NAME/KEY: modified_base
<222> LOCATION: (1)...(1)
<223> OTHER INFORMATION: n = t conjugated to biotin

<400> SEQUENCE: 7
ngtgctggag tattactgta agaaaga                                              27
```

<210> SEQ ID NO 8
<211> LENGTH: 27
<212> TYPE: DNA
<213> ORGANISM: Artificial Sequence
<220> FEATURE:
<223> OTHER INFORMATION: VR35-8 primer
<220> FEATURE:
<221> NAME/KEY: modified_base
<222> LOCATION: (1)...(1)
<223> OTHER INFORMATION: n = c conjugated to biotin

<400> SEQUENCE: 8
ngtgctggag tattactgtg cgagagg                                27

<210> SEQ ID NO 9
<211> LENGTH: 28
<212> TYPE: DNA
<213> ORGANISM: Artificial Sequence
<220> FEATURE:
<223> OTHER INFORMATION: VR33-1 primer
<220> FEATURE:
<221> NAME/KEY: modified_base
<222> LOCATION: (1)...(1)
<223> OTHER INFORMATION: n = c conjugated to biotin

<400> SEQUENCE: 9
nrgtctggag gaccagggtg cccyggcc                                28

<210> SEQ ID NO 10
<211> LENGTH: 28
<212> TYPE: DNA
<213> ORGANISM: Artificial Sequence
<220> FEATURE:
<223> OTHER INFORMATION: VR33-2 primer
<220> FEATURE:
<221> NAME/KEY: modified_base
<222> LOCATION: (1)...(1)
<223> OTHER INFORMATION: n = c conjugated to biotin

<400> SEQUENCE: 10
nggtctggag gaccattgtc ccttggcc                                28

<210> SEQ ID NO 11
<211> LENGTH: 28
<212> TYPE: DNA
<213> ORGANISM: Artificial Sequence
<220> FEATURE:
<223> OTHER INFORMATION: VR33-3 primer
<220> FEATURE:
<221> NAME/KEY: modified_base
<222> LOCATION: (1)...(1)
<223> OTHER INFORMATION: n = c conjugated to biotin

<400> SEQUENCE: 11
nggtctggag gaccagggtt ccttggcc                                28

<210> SEQ ID NO 12
<211> LENGTH: 28
<212> TYPE: DNA
<213> ORGANISM: Artificial Sequence
<220> FEATURE:
<223> OTHER INFORMATION: VR33-4 primer
<220> FEATURE:
<221> NAME/KEY: modified_base
<222> LOCATION: (1)...(1)
<223> OTHER INFORMATION: n = c conjugated to biotin

<400> SEQUENCE: 12
nggtctggag gaccgtggtc ccttggcc                                28

<210> SEQ ID NO 13
<211> LENGTH: 59
<212> TYPE: DNA
<213> ORGANISM: Artificial Sequence
<220> FEATURE:
<223> OTHER INFORMATION: adaptor 1 (GFP 4-22)

<400> SEQUENCE: 13
ggagaagaac ttttcactgg agttgtccca attcttgttg aattagatgg tgatgttag    59

<210> SEQ ID NO 14
<211> LENGTH: 57
<212> TYPE: DNA
<213> ORGANISM: Artificial Sequence
<220> FEATURE:
<223> OTHER INFORMATION: adaptor 1 (GFP 4-22)
<220> FEATURE:
<221> NAME/KEY: modified_base
<222> LOCATION: (1)...(1)
<223> OTHER INFORMATION: n = phosphorylated a

<400> SEQUENCE: 14
nacatcacca tctaattcaa caagaattgg gacaactcca gtgaaaagtt cttctcc    57

<210> SEQ ID NO 15
<211> LENGTH: 54
<212> TYPE: DNA
<213> ORGANISM: Artificial Sequence
<220> FEATURE:
<223> OTHER INFORMATION: adaptor 2 (GFP 24-42)
<220> FEATURE:
<221> NAME/KEY: modified_base
<222> LOCATION: (1)...(1)
<223> OTHER INFORMATION: n = phosphorylated g

<400> SEQUENCE: 15
nggcacaaat tttctgtcag aggagagggt gaaggtgatg ctacaacgga aaac    54

<210> SEQ ID NO 16
<211> LENGTH: 58
<212> TYPE: DNA
<213> ORGANISM: Artificial Sequence
<220> FEATURE:
<223> OTHER INFORMATION: adaptor 2 (GFP 24-42)

<400> SEQUENCE: 16
gagttttccg ttgtagcatc accttcagcc tctcctctga cagaaaattt gtgccgg    58

<210> SEQ ID NO 17
<211> LENGTH: 56
<212> TYPE: DNA
<213> ORGANISM: Artificial Sequence
<220> FEATURE:
<223> OTHER INFORMATION: adaptor 3 (GFP 85-102)

<400> SEQUENCE: 17
aagagtgcca tgcccgaagg ttatgtacag gaacgcacta tatctttcaa agatag    56

<210> SEQ ID NO 18
<211> LENGTH: 54
<212> TYPE: DNA
<213> ORGANISM: Artificial Sequence
<220> FEATURE:
<223> OTHER INFORMATION: adaptor 3 (GFP 85-102)
<220> FEATURE:
<221> NAME/KEY: modified_base
<222> LOCATION: (1)...(1)
<223> OTHER INFORMATION: n = phosphorylated a

```
<400> SEQUENCE: 18
ntctttgaaa gatatagtgc gttcctgtac ataaccttcc gggatggcac tctt            54

<210> SEQ ID NO 19
<211> LENGTH: 52
<212> TYPE: DNA
<213> ORGANISM: Artificial Sequence
<220> FEATURE:
<223> OTHER INFORMATION: adaptor 4 (GFP 103-120)
<220> FEATURE:
<221> NAME/KEY: modified_base
<222> LOCATION: (1)...(1)
<223> OTHER INFORMATION: n = phosphorylated g

<400> SEQUENCE: 19
nacgggacct acaagacgcg tgctgaagtc aagtttgaag gtgataccct tg              52

<210> SEQ ID NO 20
<211> LENGTH: 56
<212> TYPE: DNA
<213> ORGANISM: Artificial Sequence
<220> FEATURE:
<223> OTHER INFORMATION: adaptor 4 (GFP 103-120)

<400> SEQUENCE: 20
aacaagggta tcaccttcaa acttgacttc agcacgcgtc ttgtaggtcc cgtcgg          56

<210> SEQ ID NO 21
<211> LENGTH: 49
<212> TYPE: DNA
<213> ORGANISM: Artificial Sequence
<220> FEATURE:
<223> OTHER INFORMATION: adaptor 5 (GFP 163-172)

<400> SEQUENCE: 21
caaaagaatg gaatcaaagc taacttcaaa attcgccaca acgttgaag                  49

<210> SEQ ID NO 22
<211> LENGTH: 45
<212> TYPE: DNA
<213> ORGANISM: Artificial Sequence
<220> FEATURE:
<223> OTHER INFORMATION: adaptor 5 (GFP 163-172)
<220> FEATURE:
<221> NAME/KEY: modified_base
<222> LOCATION: (1)...(1)
<223> OTHER INFORMATION: n = phosphorylated t

<400> SEQUENCE: 22
ncttcgttgt ggcgaatttt gaagttagct ttgattccat tcttt                      45

<210> SEQ ID NO 23
<211> LENGTH: 47
<212> TYPE: DNA
<213> ORGANISM: Artificial Sequence
<220> FEATURE:
<223> OTHER INFORMATION: adaptor 6 (GFP 173-184)
<220> FEATURE:
<221> NAME/KEY: modified_base
<222> LOCATION: (1)...(1)
<223> OTHER INFORMATION: n = phosphorylated g

<400> SEQUENCE: 23
natggttccg ttcaactagc agaccattat caacaaaata ctccaat                    47
```

<210> SEQ ID NO 24
<211> LENGTH: 51
<212> TYPE: DNA
<213> ORGANISM: Artificial Sequence
<220> FEATURE:
<223> OTHER INFORMATION: adaptor 6 (GFP 173-184)

<400> SEQUENCE: 24
caattggagt attttgttga taatggtctg ctagttgaac ggaaccatcg g    51

<210> SEQ ID NO 25
<211> LENGTH: 67
<212> TYPE: DNA
<213> ORGANISM: Artificial Sequence
<220> FEATURE:
<223> OTHER INFORMATION: adaptor 7 (GFP 192-213)

<400> SEQUENCE: 25 cctgtcctttt taccagacaa ccattacctg tcgacacaat ctgtcctttc gaaagatccc    60
aacgaag    67

<210> SEQ ID NO 26
<211> LENGTH: 65
<212> TYPE: DNA
<213> ORGANISM: Artificial Sequence
<220> FEATURE:
<223> OTHER INFORMATION: adaptor 7 (GFP 192-213)
<220> FEATURE:
<221> NAME/KEY: modified_base
<222> LOCATION: (1)...(1)
<223> OTHER INFORMATION: n = phosphorylated t

<400> SEQUENCE: 26
ncgttgggat ctttcgaaag gacagattgt gtcgacaggt aatggttgtc tggtaaaagg    60
acagg    65

<210> SEQ ID NO 27
<211> LENGTH: 64
<212> TYPE: DNA
<213> ORGANISM: Artificial Sequence
<220> FEATURE:
<223> OTHER INFORMATION: adaptor 8 (GFP 214-235)
<220> FEATURE:
<221> NAME/KEY: modified_base
<222> LOCATION: (1)...(1)
<223> OTHER INFORMATION: n = phosphorylated a

<400> SEQUENCE: 27
nagcgtgacc acatggtcct tcttgagttt gtaactgctg ctgggattac acatggcatg    60
gatg    64

<210> SEQ ID NO 28
<211> LENGTH: 68
<212> TYPE: DNA
<213> ORGANISM: Artificial Sequence
<220> FEATURE:
<223> OTHER INFORMATION: adaptor 8 (GFP 214-235)

<400> SEQUENCE: 28
ctcatccatg ccatgtgtaa tcccagcagc agttacaaac tcaagaagga ccatgtggtc    60
acgcttgg    68

<210> SEQ ID NO 29
<211> LENGTH: 34
<212> TYPE: DNA
<213> ORGANISM: Artificial Sequence
<220> FEATURE:
<223> OTHER INFORMATION: BcgI recognition site
<220> FEATURE:
<221> NAME/KEY: misc_feature
<222> LOCATION: (1)...(34)
<223> OTHER INFORMATION: n = g, a, c or t

<400> SEQUENCE: 29
nnnnnnnnnn cgannnnnnt gcnnnnnnnn nnnn    34

<210> SEQ ID NO 30
<211> LENGTH: 34
<212> TYPE: DNA
<213> ORGANISM: Artificial Sequence
<220> FEATURE:
<223> OTHER INFORMATION: BcgI recognition site
<220> FEATURE:
<221> NAME/KEY: misc_feature
<222> LOCATION: (1)...(34)
<223> OTHER INFORMATION: n = g, a, c or t

<400> SEQUENCE: 30
nnnnnnnnnn gcannnnnnt cgnnnnnnnn nnnn    34

<210> SEQ ID NO 31
<211> LENGTH: 41
<212> TYPE: DNA
<213> ORGANISM: Artificial Sequence
<220> FEATURE:
<223> OTHER INFORMATION: 5' primer 1VHL-BcgI-5'

<400> SEQUENCE: 31
aggatcctct tyttggtggc cgaagccact gcwgcccact c    41

<210> SEQ ID NO 32
<211> LENGTH: 41
<212> TYPE: DNA
<213> ORGANISM: Artificial Sequence
<220> FEATURE:
<223> OTHER INFORMATION: 5' primer 2VHL-BcgI-5'

<400> SEQUENCE: 32
aggatcctct tcttggtggc cgaagctact gctgcccact c    41

<210> SEQ ID NO 33
<211> LENGTH: 41
<212> TYPE: DNA
<213> ORGANISM: Artificial Sequence
<220> FEATURE:
<223> OTHER INFORMATION: 5' primer 3VHL-BcgI-5'

<400> SEQUENCE: 33
agcatccttt tcttggtggc cgaaccaact gctgcccact c    41

<210> SEQ ID NO 34
<211> LENGTH: 41
<212> TYPE: DNA
<213> ORGANISM: Artificial Sequence
<220> FEATURE:
<223> OTHER INFORMATION: 5' primer 4VHL-BcgI-5'

<400> SEQUENCE: 34
aggatcctct tcttggtggc cgaagctact gccacccacg c    41

<210> SEQ ID NO 35
<211> LENGTH: 41
<212> TYPE: DNA
<213> ORGANISM: Artificial Sequence
<220> FEATURE:
<223> OTHER INFORMATION: 5' primer 5VHL-BcgI-5'

<400> SEQUENCE: 35
agaatcctct tcttggtggc cgaagccact gctgcctact c        41

<210> SEQ ID NO 36
<211> LENGTH: 41
<212> TYPE: DNA
<213> ORGANISM: Artificial Sequence
<220> FEATURE:
<223> OTHER INFORMATION: 5' primer 6VHL-BcgI-5'

<400> SEQUENCE: 36
agggtcttct gcttgctggc cgaagctcct gctgctcact c        41

<210> SEQ ID NO 37
<211> LENGTH: 41
<212> TYPE: DNA
<213> ORGANISM: Artificial Sequence
<220> FEATURE:
<223> OTHER INFORMATION: 5' primer 7VHL-BcgI-5'

<400> SEQUENCE: 37
aggatcctct tcttggtggg cgaagcgact gctgcccact c        41

<210> SEQ ID NO 38
<211> LENGTH: 41
<212> TYPE: DNA
<213> ORGANISM: Artificial Sequence
<220> FEATURE:
<223> OTHER INFORMATION: 5' primer 8VHL-BcgI-5'

<400> SEQUENCE: 38
tccacgctcc tgctgctgac cgacccttct gcggtcttgt c        41

<210> SEQ ID NO 39
<211> LENGTH: 41
<212> TYPE: DNA
<213> ORGANISM: Artificial Sequence
<220> FEATURE:
<223> OTHER INFORMATION: 5' primer 9VHL-BcgI-5'

<400> SEQUENCE: 39
tacacactcc tgctgctgac cgacccttct gcggtcttgt c        41

<210> SEQ ID NO 40
<211> LENGTH: 41
<212> TYPE: DNA
<213> ORGANISM: Artificial Sequence
<220> FEATURE:
<223> OTHER INFORMATION: 5' primer 10VHL-BcgI-5'

<400> SEQUENCE: 40
hgctgggttt tccttgttgc cgatttarat gctgtccagt g        41

<210> SEQ ID NO 41
<211> LENGTH: 41
<212> TYPE: DNA
<213> ORGANISM: Artificial Sequence
<220> FEATURE:
<223> OTHER INFORMATION: 5' primer 11VHL-BcgI-5'

```
<400> SEQUENCE: 41
agctgggttt tccttgttgc cgatwtaaat gctgtccart g                    41

<210> SEQ ID NO 42
<211> LENGTH: 41
<212> TYPE: DNA
<213> ORGANISM: Artificial Sequence
<220> FEATURE:
<223> OTHER INFORMATION: 5' primer 12VHL-BcgI-5'

<400> SEQUENCE: 42
agctggattt tccttgctgc cgatttaaat gctgtccagt g                    41

<210> SEQ ID NO 43
<211> LENGTH: 41
<212> TYPE: DNA
<213> ORGANISM: Artificial Sequence
<220> FEATURE:
<223> OTHER INFORMATION: 5' primer 13VHL-BcgI-5'

<400> SEQUENCE: 43
agctggattt tcctttggc cgatttaaat gctgtccagt g                     41

<210> SEQ ID NO 44
<211> LENGTH: 41
<212> TYPE: DNA
<213> ORGANISM: Artificial Sequence
<220> FEATURE:
<223> OTHER INFORMATION: 5' primer 14VHL-BcgI-5'

<400> SEQUENCE: 44
agctggcttt ttcttgtggc cgatttaaat gctgtccagt g                    41

<210> SEQ ID NO 45
<211> LENGTH: 41
<212> TYPE: DNA
<213> ORGANISM: Artificial Sequence
<220> FEATURE:
<223> OTHER INFORMATION: 5' primer 15VHL-BcgI-5'

<400> SEQUENCE: 45
agctgggttt tccttgttgc cgattttaat gctgtccagt g                    41

<210> SEQ ID NO 46
<211> LENGTH: 41
<212> TYPE: DNA
<213> ORGANISM: Artificial Sequence
<220> FEATURE:
<223> OTHER INFORMATION: 5' primer 16VHL-BcgI-5'

<400> SEQUENCE: 46
agctgggttt tcctcgttgc cgatttaagt gctgtccagt g                    41

<210> SEQ ID NO 47
<211> LENGTH: 41
<212> TYPE: DNA
<213> ORGANISM: Artificial Sequence
<220> FEATURE:
<223> OTHER INFORMATION: 5' primer 17VHL-BcgI-5'

<400> SEQUENCE: 47
agctgggttt tccttgttgc cgaattagat gctgtccagt g                    41
```

<210> SEQ ID NO 48
<211> LENGTH: 41
<212> TYPE: DNA
<213> ORGANISM: Artificial Sequence
<220> FEATURE:
<223> OTHER INFORMATION: 5' primer 18VHL-BcgI-5'

<400> SEQUENCE: 48
agctgggttt tccttgttgt cgatttacat gctgtccagt g                41

<210> SEQ ID NO 49
<211> LENGTH: 41
<212> TYPE: DNA
<213> ORGANISM: Artificial Sequence
<220> FEATURE:
<223> OTHER INFORMATION: 5' primer 19VHL-BcgI-5'

<400> SEQUENCE: 49
ttyttcctcc tgctggtggc cgatcccagt gcggtcctgy c                41

<210> SEQ ID NO 50
<211> LENGTH: 41
<212> TYPE: DNA
<213> ORGANISM: Artificial Sequence
<220> FEATURE:
<223> OTHER INFORMATION: 5' primer 20VHL-BcgI-5'

<400> SEQUENCE: 50
ttcttcctyc tcctggtggc cgatcccagt gcggtcctgt c                41

<210> SEQ ID NO 51
<211> LENGTH: 41
<212> TYPE: DNA
<213> ORGANISM: Artificial Sequence
<220> FEATURE:
<223> OTHER INFORMATION: 5' primer 21VHL-BcgI-5'

<400> SEQUENCE: 51
atcctcgccc tcctcctggc cgatctccat gcagtctgtt c                41

<210> SEQ ID NO 52
<211> LENGTH: 41
<212> TYPE: DNA
<213> ORGANISM: Artificial Sequence
<220> FEATURE:
<223> OTHER INFORMATION: 5' primer 22VHL-BcgI-5'

<400> SEQUENCE: 52
atccttggcc tcctcctggc cgatctccat gcagtctgtg c                41

<210> SEQ ID NO 53
<211> LENGTH: 41
<212> TYPE: DNA
<213> ORGANISM: Artificial Sequence
<220> FEATURE:
<223> OTHER INFORMATION: 5' primer 23VHL-BcgI-5'

<400> SEQUENCE: 53
atcttcctgc ccgtgctggg cgacccatgt gctgtcctgt c                41

<210> SEQ ID NO 54
<211> LENGTH: 41
<212> TYPE: DNA
<213> ORGANISM: Artificial Sequence
<220> FEATURE:
<223> OTHER INFORMATION: 5' primer 24VHL-BcgI-5'

```
<400> SEQUENCE: 54
aggatcctct tcttggtggc cgaagcaact gctgcccact c                41

<210> SEQ ID NO 55
<211> LENGTH: 41
<212> TYPE: DNA
<213> ORGANISM: Artificial Sequence
<220> FEATURE:
<223> OTHER INFORMATION: IgG 3' primer, sense

<400> SEQUENCE: 55
cctccaccac gagcccattg ctcttccccc tggcaccctc c                41

<210> SEQ ID NO 56
<211> LENGTH: 41
<212> TYPE: DNA
<213> ORGANISM: Artificial Sequence
<220> FEATURE:
<223> OTHER INFORMATION: IgG 3' primer, sense

<400> SEQUENCE: 56
cytccaccac gagcccattg ctcttccccc tggcgccctg c                41

<210> SEQ ID NO 57
<211> LENGTH: 41
<212> TYPE: DNA
<213> ORGANISM: Artificial Sequence
<220> FEATURE:
<223> OTHER INFORMATION: IgM 3' primer, sense

<400> SEQUENCE: 57
ggagtgcatc gaccccaatg cttttccccc tcgtctcctg t                41

<210> SEQ ID NO 58
<211> LENGTH: 41
<212> TYPE: DNA
<213> ORGANISM: Artificial Sequence
<220> FEATURE:
<223> OTHER INFORMATION: IgG 3' primer 1IgG-BcgI-3', anti-sense

<400> SEQUENCE: 58
ggaggtggtg ctcgggtaac gagaaggggg accgtgggag g                41

<210> SEQ ID NO 59
<211> LENGTH: 41
<212> TYPE: DNA
<213> ORGANISM: Artificial Sequence
<220> FEATURE:
<223> OTHER INFORMATION: IgG 3' primer 2IgG-BcgI-3', anti-sense

<400> SEQUENCE: 59
graggtggtg ctcgggtaac gagaaggggg accgcgggac g                41

<210> SEQ ID NO 60
<211> LENGTH: 41
<212> TYPE: DNA
<213> ORGANISM: Artificial Sequence
<220> FEATURE:
<223> OTHER INFORMATION: IgM 3' primer 1IgM-BcgI-3', anti-sense

<400> SEQUENCE: 60
cctcacgtag ctggggttac gaaaaggggg agcagaggac a                41
```

```
<210> SEQ ID NO 61
<211> LENGTH: 48
<212> TYPE: DNA
<213> ORGANISM: Artificial Sequence
<220> FEATURE:
<223> OTHER INFORMATION: 5' end amplified V-H gene structure PCR product
<220> FEATURE:
<221> NAME/KEY: misc_feature
<222> LOCATION: (45)...(48)
<223> OTHER INFORMATION: n = g, a, c or t

<400> SEQUENCE: 61
aggatcctct tyttggtggc cgaagccact gcwgcccact ccgannnn            48

<210> SEQ ID NO 62
<211> LENGTH: 48
<212> TYPE: DNA
<213> ORGANISM: Artificial Sequence
<220> FEATURE:
<223> OTHER INFORMATION: 3' end amplified V-H gene structure PCR product
<220> FEATURE:
<221> NAME/KEY: misc_feature
<222> LOCATION: (1)...(3)
<223> OTHER INFORMATION: n = g, a, c or t

<400> SEQUENCE: 62
nnntcaggga gtgcatcgac cccaatgctt ttcccctcg tctcctgt              48

<210> SEQ ID NO 63
<211> LENGTH: 25
<212> TYPE: DNA
<213> ORGANISM: Artificial Sequence
<220> FEATURE:
<223> OTHER INFORMATION: 5' end primer
<220> FEATURE:
<221> NAME/KEY: modified_base
<222> LOCATION: (1)...(1)
<223> OTHER INFORMATION: n = phosphorylated a

<400> SEQUENCE: 63
ngccatggcg agctcctatt gaagc                                      25

<210> SEQ ID NO 64
<211> LENGTH: 27
<212> TYPE: DNA
<213> ORGANISM: Artificial Sequence
<220> FEATURE:
<223> OTHER INFORMATION: 5' end primer complement

<400> SEQUENCE: 64
atatgcttca ataggagctc gccatgg                                    27

<210> SEQ ID NO 65
<211> LENGTH: 25
<212> TYPE: DNA
<213> ORGANISM: Artificial Sequence
<220> FEATURE:
<223> OTHER INFORMATION: 5' end primer
<220> FEATURE:
<221> NAME/KEY: modified_base
<222> LOCATION: (1)...(1)
<223> OTHER INFORMATION: n = phosphorylated a

<400> SEQUENCE: 65
ncccatggcg agctcctatt gaagc                                      25
```

```
<210> SEQ ID NO 66
<211> LENGTH: 6
<212> TYPE: PRT
<213> ORGANISM: Artificial Sequence
<220> FEATURE:
<223> OTHER INFORMATION: 6His tag

<400> SEQUENCE: 66

His His His His His His
 1               5

<210> SEQ ID NO 67
<211> LENGTH: 28
<212> TYPE: DNA
<213> ORGANISM: Artificial Sequence
<220> FEATURE:
<223> OTHER INFORMATION: 3' end primer complement

<400> SEQUENCE: 67
cacccaaacc ctaaccaaac ggcgatcg                                          28

<210> SEQ ID NO 68
<211> LENGTH: 27
<212> TYPE: DNA
<213> ORGANISM: Artificial Sequence
<220> FEATURE:
<223> OTHER INFORMATION: 3' end primer
<220> FEATURE:
<221> NAME/KEY: modified_base
<222> LOCATION: (1)...(1)
<223> OTHER INFORMATION: n = phosphorylated g

<400> SEQUENCE: 68
ntcgatcgcc gtttggttag ggtttgg                                           27

<210> SEQ ID NO 69
<211> LENGTH: 29
<212> TYPE: DNA
<213> ORGANISM: Artificial Sequence
<220> FEATURE:
<223> OTHER INFORMATION: VH structure after removal of unligated 5'
      adaptors
<220> FEATURE:
<221> NAME/KEY: misc_feature
<222> LOCATION: (26)...(29)
<223> OTHER INFORMATION: n = g, a, c or t

<400> SEQUENCE: 69
cgaagttatc ctcgagcggt acccannnn                                         29

<210> SEQ ID NO 70
<211> LENGTH: 34
<212> TYPE: DNA
<213> ORGANISM: Artificial Sequence
<220> FEATURE:
<223> OTHER INFORMATION: VH structure after removal of unligated 5'
      adaptors
<220> FEATURE:
<221> NAME/KEY: misc_feature
<222> LOCATION: (1)...(3)
<223> OTHER INFORMATION: n = g, a, c or t

<400> SEQUENCE: 70
nnntcagcta gcggcaaacc aatcccaaac ccac                                   34

<210> SEQ ID NO 71
<211> LENGTH: 33
<212> TYPE: DNA
<213> ORGANISM: Artificial Sequence
```

```
<220> FEATURE:
<223> OTHER INFORMATION: VH structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 71
nnnntgggta ccgctcgagg ataacttcgt ata                                 33

<210> SEQ ID NO 72
<211> LENGTH: 31
<212> TYPE: DNA
<213> ORGANISM: Artificial Sequence
<220> FEATURE:
<223> OTHER INFORMATION: VH structure after removal of unligated 5'
      adaptors
<220> FEATURE:
<221> NAME/KEY: misc_feature
<222> LOCATION: (29)...(31)
<223> OTHER INFORMATION: n = g, a, c or t

<400> SEQUENCE: 72
ggtttgggat tggtttgccg ctagctgann n                                   31

<210> SEQ ID NO 73
<211> LENGTH: 29
<212> TYPE: DNA
<213> ORGANISM: Artificial Sequence
<220> FEATURE:
<223> OTHER INFORMATION: VH structure after removal of unligated 5'
      adaptors
<220> FEATURE:
<221> NAME/KEY: misc_feature
<222> LOCATION: (26)...(29)
<223> OTHER INFORMATION: n = g, a, c or t

<400> SEQUENCE: 73
cgaagttatc ctcgagcggt accgannnn                                      29

<210> SEQ ID NO 74
<211> LENGTH: 33
<212> TYPE: DNA
<213> ORGANISM: Artificial Sequence
<220> FEATURE:
<223> OTHER INFORMATION: VH structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 74
nnnntcggta ccgctcgagg ataacttcgt ata                                 33

<210> SEQ ID NO 75
<211> LENGTH: 17
<212> TYPE: DNA
<213> ORGANISM: Artificial Sequence
<220> FEATURE:
<223> OTHER INFORMATION: 5' VH linker

<400> SEQUENCE: 75
tactatacga agttatc                                                   17
```

<210> SEQ ID NO 76
<211> LENGTH: 17
<212> TYPE: DNA
<213> ORGANISM: Artificial Sequence
<220> FEATURE:
<223> OTHER INFORMATION: 3' VH linker

<400> SEQUENCE: 76
gtggtttggg attggtt                                              17

<210> SEQ ID NO 77
<211> LENGTH: 18
<212> TYPE: DNA
<213> ORGANISM: Artificial Sequence
<220> FEATURE:
<223> OTHER INFORMATION: amplified VH cleaved with XhoI and NheI
<220> FEATURE:
<221> NAME/KEY: misc_feature
<222> LOCATION: (15)...(8)
<223> OTHER INFORMATION: n = g, a, c or t

<400> SEQUENCE: 77
tcgagcggta ccsannnn                                             18

<210> SEQ ID NO 78
<211> LENGTH: 14
<212> TYPE: DNA
<213> ORGANISM: Artificial Sequence
<220> FEATURE:
<223> OTHER INFORMATION: amplified VH cleaved with XhoI and NheI
<220> FEATURE:
<221> NAME/KEY: misc_feature
<222> LOCATION: (1)...(1)
<223> OTHER INFORMATION: n = g, a, c or t

<400> SEQUENCE: 78
nnnntsggta ccgc                                                 14

<210> SEQ ID NO 79
<211> LENGTH: 11
<212> TYPE: DNA
<213> ORGANISM: Artificial Sequence
<220> FEATURE:
<223> OTHER INFORMATION: amplified VH cleaved with XhoI and NheI
<220> FEATURE:
<221> NAME/KEY: misc_feature
<222> LOCATION: (9)...(11)
<223> OTHER INFORMATION: n = g, a, c or t

<400> SEQUENCE: 79
ctagctgann n                                                    11

<210> SEQ ID NO 80
<211> LENGTH: 41
<212> TYPE: DNA
<213> ORGANISM: Artificial Sequence
<220> FEATURE:
<223> OTHER INFORMATION: 5' primer 1VKL-BcgI-5'

<400> SEQUENCE: 80
ctcctggggc tcctgctact cgagctccgt gctgccagat g                   41

<210> SEQ ID NO 81
<211> LENGTH: 41
<212> TYPE: DNA
<213> ORGANISM: Artificial Sequence
<220> FEATURE:
<223> OTHER INFORMATION: 5' primer 2VKL-BcgI-5'

<400> SEQUENCE: 81
ctcctggggc tcctgcwgct cgagctcyct gctgccagat g        41

<210> SEQ ID NO 82
<211> LENGTH: 41
<212> TYPE: DNA
<213> ORGANISM: Artificial Sequence
<220> FEATURE:
<223> OTHER INFORMATION: 5' primer 3VKL-BcgI-5'

<400> SEQUENCE: 82
ctcctgggac tcctgctgct cgagctccct gctaccagat g        41

<210> SEQ ID NO 83
<211> LENGTH: 41
<212> TYPE: DNA
<213> ORGANISM: Artificial Sequence
<220> FEATURE:
<223> OTHER INFORMATION: 5' primer 4VKL-BcgI-5'

<400> SEQUENCE: 83
ctcctggggc tcctgctgct cgagttccct gctkccagrt g        41

<210> SEQ ID NO 84
<211> LENGTH: 41
<212> TYPE: DNA
<213> ORGANISM: Artificial Sequence
<220> FEATURE:
<223> OTHER INFORMATION: 5' primer 5VKL-BcgI-5'

<400> SEQUENCE: 84
ckcctggggc tcctgctgct cgakttccct gctgccagat g        41

<210> SEQ ID NO 85
<211> LENGTH: 41
<212> TYPE: DNA
<213> ORGANISM: Artificial Sequence
<220> FEATURE:
<223> OTHER INFORMATION: 5' primer 6VKL-BcgI-5'

<400> SEQUENCE: 85
ctcctggggc tyctgctgct cgagctccct gctgccarat g        41

<210> SEQ ID NO 86
<211> LENGTH: 41
<212> TYPE: DNA
<213> ORGANISM: Artificial Sequence
<220> FEATURE:
<223> OTHER INFORMATION: 5' primer 7VKL-BcgI-5'

<400> SEQUENCE: 86
ctcctggggc tgctaatgct cgaggtccct gcatccagtg r        41

<210> SEQ ID NO 87
<211> LENGTH: 41
<212> TYPE: DNA
<213> ORGANISM: Artificial Sequence
<220> FEATURE:
<223> OTHER INFORMATION: 5' primer 8VKL-BcgI-5'

<400> SEQUENCE: 87
ctcctggggc tgctaatgct cgagatmcct gcatccagtg c        41

```
<210> SEQ ID NO 88
<211> LENGTH: 41
<212> TYPE: DNA
<213> ORGANISM: Artificial Sequence
<220> FEATURE:
<223> OTHER INFORMATION: 5' primer 9VKL-BcgI-5'

<400> SEQUENCE: 88
ctyctggggc tgctaatgct cgaggtcyct gcatccagtg g       41

<210> SEQ ID NO 89
<211> LENGTH: 41
<212> TYPE: DNA
<213> ORGANISM: Artificial Sequence
<220> FEATURE:
<223> OTHER INFORMATION: 5' primer 10VKL-BcgI-5'

<400> SEQUENCE: 89
cttctcttcc tcctgctact cgagctcmct gctaccacyg g       41

<210> SEQ ID NO 90
<211> LENGTH: 41
<212> TYPE: DNA
<213> ORGANISM: Artificial Sequence
<220> FEATURE:
<223> OTHER INFORMATION: 5' primer 11VKL-BcgI-5'

<400> SEQUENCE: 90
ttcttcttcc tcctgctact cgagctccct gctaccaccg g       41

<210> SEQ ID NO 91
<211> LENGTH: 41
<212> TYPE: DNA
<213> ORGANISM: Artificial Sequence
<220> FEATURE:
<223> OTHER INFORMATION: 5' primer 12VKL-BcgI-5'

<400> SEQUENCE: 91
gtcttcattt ctctgttgct cgagatctct gctgcctacg g       41

<210> SEQ ID NO 92
<211> LENGTH: 41
<212> TYPE: DNA
<213> ORGANISM: Artificial Sequence
<220> FEATURE:
<223> OTHER INFORMATION: 5' primer 13VKL-BcgI-5'

<400> SEQUENCE: 92
ctcctcagct tcctcctcct cgagatctct gctaccaggg c       41

<210> SEQ ID NO 93
<211> LENGTH: 41
<212> TYPE: DNA
<213> ORGANISM: Artificial Sequence
<220> FEATURE:
<223> OTHER INFORMATION: 5' primer 14VKL-BcgI-5'

<400> SEQUENCE: 93
ctcattgggt ttctgctgct cgaggttcct gcctccaggg g       41

<210> SEQ ID NO 94
<211> LENGTH: 41
<212> TYPE: DNA
<213> ORGANISM: Artificial Sequence
<220> FEATURE:
<223> OTHER INFORMATION: 5' primer 15VKL-BcgI-5'
```

-continued

```
<400> SEQUENCE: 94
ttcctgcggc ttctgctcct cgaggttcct gcctccaggg g                           41

<210> SEQ ID NO 95
<211> LENGTH: 41
<212> TYPE: DNA
<213> ORGANISM: Artificial Sequence
<220> FEATURE:
<223> OTHER INFORMATION: 3' CK primer, sense

<400> SEQUENCE: 95
gaactgtggc gacaccattg ctcttcatct tcccgccatc t                           41

<210> SEQ ID NO 96
<211> LENGTH: 41
<212> TYPE: DNA
<213> ORGANISM: Artificial Sequence
<220> FEATURE:
<223> OTHER INFORMATION: 3' CK primer 1CK-BcgI-3', anti-sense

<400> SEQUENCE: 96
cttgacaccg ctgtggtaac gagaagtaga agggcggtag a                           41

<210> SEQ ID NO 97
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated a

<400> SEQUENCE: 97
ngccgtacgc gcggcgaacg acg                                               23

<210> SEQ ID NO 98
<211> LENGTH: 24
<212> TYPE: DNA
<213> ORGANISM: Artificial Sequence
<220> FEATURE:
<223> OTHER INFORMATION: 5' end adaptor primer complement

<400> SEQUENCE: 98
gagcgtcgtt cgccgcgcgt acgg                                              24

<210> SEQ ID NO 99
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated a

<400> SEQUENCE: 99
naccgtacgc gcggcgaacg acg                                               23

<210> SEQ ID NO 100
<211> LENGTH: 23
<212> TYPE: DNA
<213> ORGANISM: Artificial Sequence
<220> FEATURE:
<223> OTHER INFORMATION: 5' end adaptor primer
```

```
<220> FEATURE:
<221> NAME/KEY: modified_base
<222> LOCATION: (1)...(1)
<223> OTHER INFORMATION: n = phosphorylated c

<400> SEQUENCE: 100
ngccgtacgc gcggcgaacg acg                                              23

<210> SEQ ID NO 101
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated t

<400> SEQUENCE: 101
ngccgtacgc gcggcgaacg acg                                              23

<210> SEQ ID NO 102
<211> LENGTH: 26
<212> TYPE: DNA
<213> ORGANISM: Artificial Sequence
<220> FEATURE:
<223> OTHER INFORMATION: 3' end adaptor primer complement

<400> SEQUENCE: 102
atgcttcaat accagctggg aggcct                                           26

<210> SEQ ID NO 103
<211> LENGTH: 23
<212> TYPE: DNA
<213> ORGANISM: Artificial Sequence
<220> FEATURE:
<223> OTHER INFORMATION: 3' end adaptor primer
<220> FEATURE:
<221> NAME/KEY: modified_base
<222> LOCATION: (1)...(1)
<223> OTHER INFORMATION: n = phosphorylated t

<400> SEQUENCE: 103
ntaggcctcc cagctggtat tga                                              23

<210> SEQ ID NO 104
<211> LENGTH: 27
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (24)...(27)
<223> OTHER INFORMATION: n = g, a, c or t

<400> SEQUENCE: 104
gcagcaagcg gcgcgcatgc cgannnn                                          27

<210> SEQ ID NO 105
<211> LENGTH: 32
<212> TYPE: DNA
<213> ORGANISM: Artificial Sequence
<220> FEATURE:
<223> OTHER INFORMATION: VK structure after removal of unligated 5'
      adaptors
```

```
<220> FEATURE:
<221> NAME/KEY: misc_feature
<222> LOCATION: (1)...(3)
<223> OTHER INFORMATION: n = g, a, c or t

<400> SEQUENCE: 105
nnnaaatccg agggtcgac cataacttcg ta                                        32

<210> SEQ ID NO 106
<211> LENGTH: 30
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 106
nnnntcggca tgcgcgccgc ttgctgcgag                                          30

<210> SEQ ID NO 107
<211> LENGTH: 27
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (24)...(27)
<223> OTHER INFORMATION: n = g, a, c or t

<400> SEQUENCE: 107
agttatggtc gaccctccgg atttnnn                                             27

<210> SEQ ID NO 108
<211> LENGTH: 27
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (24)...(27)
<223> OTHER INFORMATION: n = g, a, c or t

<400> SEQUENCE: 108
gcagcaagcg gcgcgcatgc caannnn                                             27

<210> SEQ ID NO 109
<211> LENGTH: 30
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 109
nnnnttggca tgcgcgccgc ttgctgcgag                                          30
```

<210> SEQ ID NO 110
<211> LENGTH: 27
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (24)...(27)
<223> OTHER INFORMATION: n = g, a, c or t

<400> SEQUENCE: 110
gcagcaagcg gcgcgcatgc cgcnnnn                                          27

<210> SEQ ID NO 111
<211> LENGTH: 30
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 111
nnnngcggca tgcgcgccgc ttgctgcgag                                       30

<210> SEQ ID NO 112
<211> LENGTH: 27
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (24)...(27)
<223> OTHER INFORMATION: n = g, a, c or t

<400> SEQUENCE: 112
gcagcaagcg gcgcgcatgc cgtnnnn                                          27

<210> SEQ ID NO 113
<211> LENGTH: 30
<212> TYPE: DNA
<213> ORGANISM: Artificial Sequence
<220> FEATURE:
<223> OTHER INFORMATION: VK structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 113
nnnnacggca tgcgcgccgc ttgctgcgag                                       30

<210> SEQ ID NO 114
<211> LENGTH: 17
<212> TYPE: DNA
<213> ORGANISM: Artificial Sequence
<220> FEATURE:
<223> OTHER INFORMATION: 5' VL linker primer

<400> SEQUENCE: 114
gcagcaagcg gcgcgca                                                     17

```
<210> SEQ ID NO 115
<211> LENGTH: 20
<212> TYPE: DNA
<213> ORGANISM: Artificial Sequence
<220> FEATURE:
<223> OTHER INFORMATION: 3' VL linker primer

<400> SEQUENCE: 115
cgaagttatg gtcgaccctc                                               20

<210> SEQ ID NO 116
<211> LENGTH: 16
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 116
cgcgcatgcc gannnn                                                   16

<210> SEQ ID NO 117
<211> LENGTH: 15
<212> TYPE: DNA
<213> ORGANISM: Artificial Sequence
<220> FEATURE:
<223> OTHER INFORMATION: amplified VK cleaved by BssHII and SalI
<220> FEATURE:
<221> NAME/KEY: misc_feature
<222> LOCATION: (1)...(3)
<223> OTHER INFORMATION: n = g, a, c or t

<400> SEQUENCE: 117
nnnaaatccg gaggg                                                    15

<210> SEQ ID NO 118
<211> LENGTH: 12
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 118
nnnntcggca tg                                                       12

<210> SEQ ID NO 119
<211> LENGTH: 19
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (17)...(19)
<223> OTHER INFORMATION: n = g, a, c or t

<400> SEQUENCE: 119
tcgaccctcc ggatttnnn                                                19
```

<210> SEQ ID NO 120
<211> LENGTH: 16
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 120
cgcgcatgcc aannnn                                                16

<210> SEQ ID NO 121
<211> LENGTH: 12
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 121
nnnnttggca tg                                                    12

<210> SEQ ID NO 122
<211> LENGTH: 16
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 122
cgcgcatgcc gcnnnn                                                16

<210> SEQ ID NO 123
<211> LENGTH: 12
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 123
nnnngcggca tg                                                    12

<210> SEQ ID NO 124
<211> LENGTH: 16
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 124
cgcgcatgcc gtnnnn                                                16

<210> SEQ ID NO 125
<211> LENGTH: 12
<212> TYPE: DNA
<213> ORGANISM: Artificial Sequence
<220> FEATURE:
<223> OTHER INFORMATION: amplified VK cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 125
nnnnacggca tg                                                         12

<210> SEQ ID NO 126
<211> LENGTH: 41
<212> TYPE: DNA
<213> ORGANISM: Artificial Sequence
<220> FEATURE:
<223> OTHER INFORMATION: 5' primer 1VLL-BcgI-5'

<400> SEQUENCE: 126
ctcytcctca ccctcmtcac cgactgtgct gcgtcctggg c                         41

<210> SEQ ID NO 127
<211> LENGTH: 41
<212> TYPE: DNA
<213> ORGANISM: Artificial Sequence
<220> FEATURE:
<223> OTHER INFORMATION: 5' primer 2VLL-BcgI-5'

<400> SEQUENCE: 127
ctcctcctca ctctcctcgc cgactgcact gcgtcctggg c                         41

<210> SEQ ID NO 128
<211> LENGTH: 41
<212> TYPE: DNA
<213> ORGANISM: Artificial Sequence
<220> FEATURE:
<223> OTHER INFORMATION: 5' primer 3VLL-BcgI-5'

<400> SEQUENCE: 128
ctcctcctca cccttctcat cgactgcact gcgtcctggg c                         41

<210> SEQ ID NO 129
<211> LENGTH: 41
<212> TYPE: DNA
<213> ORGANISM: Artificial Sequence
<220> FEATURE:
<223> OTHER INFORMATION: 5' primer 4VLL-BcgI-5'

<400> SEQUENCE: 129
ctcctcctca scctcctcac cgagggcact gcrtcctggg c                         41

<210> SEQ ID NO 130
<211> LENGTH: 41
<212> TYPE: DNA
<213> ORGANISM: Artificial Sequence
<220> FEATURE:
<223> OTHER INFORMATION: 5' primer 5VLL-BcgI-5'

<400> SEQUENCE: 130
ctgctcctca cyctcctcac cgaggrcact gcgtcctggg c                         41

```
<210> SEQ ID NO 131
<211> LENGTH: 41
<212> TYPE: DNA
<213> ORGANISM: Artificial Sequence
<220> FEATURE:
<223> OTHER INFORMATION: 5' primer 6VLL-BcgI-5'

<400> SEQUENCE: 131
ctcttcctcg gcgtccttgc cgactgcact gcatccgtgg c          41

<210> SEQ ID NO 132
<211> LENGTH: 41
<212> TYPE: DNA
<213> ORGANISM: Artificial Sequence
<220> FEATURE:
<223> OTHER INFORMATION: 5' primer 7VLL-BcgI-5'

<400> SEQUENCE: 132
ctccttctga gcctccttgc cgactttact gcttctgtgg c          41

<210> SEQ ID NO 133
<211> LENGTH: 41
<212> TYPE: DNA
<213> ORGANISM: Artificial Sequence
<220> FEATURE:
<223> OTHER INFORMATION: 5' primer 8VLL-BcgI-5'

<400> SEQUENCE: 133
ctmctkctcc ccctcctcac cgactgcact gcctctgagg c          41

<210> SEQ ID NO 134
<211> LENGTH: 41
<212> TYPE: DNA
<213> ORGANISM: Artificial Sequence
<220> FEATURE:
<223> OTHER INFORMATION: 5' primer 9VLL-BcgI-5'

<400> SEQUENCE: 134
ctctggctca ctctcctcac cgattgcatt gcttctgtgg t          41

<210> SEQ ID NO 135
<211> LENGTH: 41
<212> TYPE: DNA
<213> ORGANISM: Artificial Sequence
<220> FEATURE:
<223> OTHER INFORMATION: 5' primer 10VLL-BcgI-5'

<400> SEQUENCE: 135
ctcctcctcg gcctcctctc cgactgcact gcctctgtga c          41

<210> SEQ ID NO 136
<211> LENGTH: 41
<212> TYPE: DNA
<213> ORGANISM: Artificial Sequence
<220> FEATURE:
<223> OTHER INFORMATION: 5' primer 11VLL-BcgI-5'

<400> SEQUENCE: 136
ctcctgctcc cactcctcaa cgactacact gcctctattg c          41

<210> SEQ ID NO 137
<211> LENGTH: 41
<212> TYPE: DNA
<213> ORGANISM: Artificial Sequence
<220> FEATURE:
<223> OTHER INFORMATION: 5' primer 12VLL-BcgI-5'
```

-continued

<400> SEQUENCE: 137
ctcctgctcc ccctcctcat cgactgcact gcctctgtgg c  41

<210> SEQ ID NO 138
<211> LENGTH: 41
<212> TYPE: DNA
<213> ORGANISM: Artificial Sequence
<220> FEATURE:
<223> OTHER INFORMATION: 5' primer 13VLL-BcgI-5'

<400> SEQUENCE: 138
ttctacctac tgcccttcat cgactccact gctctctgtg c  41

<210> SEQ ID NO 139
<211> LENGTH: 41
<212> TYPE: DNA
<213> ORGANISM: Artificial Sequence
<220> FEATURE:
<223> OTHER INFORMATION: 5' primer 14VLL-BcgI-5'

<400> SEQUENCE: 139
ctcctcttcc ctctcctcct cgactggact gcgtctctct c  41

<210> SEQ ID NO 140
<211> LENGTH: 41
<212> TYPE: DNA
<213> ORGANISM: Artificial Sequence
<220> FEATURE:
<223> OTHER INFORMATION: 5' primer 15VLL-BcgI-5'

<400> SEQUENCE: 140
ctcttcctca ccctcctcct cgactgcact gcgtctctct c  41

<210> SEQ ID NO 141
<211> LENGTH: 41
<212> TYPE: DNA
<213> ORGANISM: Artificial Sequence
<220> FEATURE:
<223> OTHER INFORMATION: 5' primer 16VLL-BcgI-5'

<400> SEQUENCE: 141
ctycttctck tgctcctctc cgactgcact gcttccctct c  41

<210> SEQ ID NO 142
<211> LENGTH: 41
<212> TYPE: DNA
<213> ORGANISM: Artificial Sequence
<220> FEATURE:
<223> OTHER INFORMATION: 5' primer 17VLL-BcgI-5'

<400> SEQUENCE: 142
ctcctcctcc tgttcctctc cgactgcact gcttccctct c  41

<210> SEQ ID NO 143
<211> LENGTH: 41
<212> TYPE: DNA
<213> ORGANISM: Artificial Sequence
<220> FEATURE:
<223> OTHER INFORMATION: 5' primer 18VLL-BcgI-5'

<400> SEQUENCE: 143
ctacttctca ccctcctcgc cgactgcact gcttcttggg c  41

```
<210> SEQ ID NO 144
<211> LENGTH: 41
<212> TYPE: DNA
<213> ORGANISM: Artificial Sequence
<220> FEATURE:
<223> OTHER INFORMATION: 5' primer 19VLL-BcgI-5'

<400> SEQUENCE: 144
ctctttctgt tcctcctcac cgactgccct gcgtccaatt c         41

<210> SEQ ID NO 145
<211> LENGTH: 41
<212> TYPE: DNA
<213> ORGANISM: Artificial Sequence
<220> FEATURE:
<223> OTHER INFORMATION: 5' primer 20VLL-BcgI-5'

<400> SEQUENCE: 145
cttctcctcg gactccttgc cgatggatct gcagtggatt c         41

<210> SEQ ID NO 146
<211> LENGTH: 41
<212> TYPE: DNA
<213> ORGANISM: Artificial Sequence
<220> FEATURE:
<223> OTHER INFORMATION: 5' primer 21VLL-BcgI-5'

<400> SEQUENCE: 146
ctgctcctca ccctcctcag cgacctcact gcgtccctct c         41

<210> SEQ ID NO 147
<211> LENGTH: 41
<212> TYPE: DNA
<213> ORGANISM: Artificial Sequence
<220> FEATURE:
<223> OTHER INFORMATION: 5' primer 22VLL-BcgI-5'

<400> SEQUENCE: 147
ctcctcctga ccctcctcac cgactctgct gcgtcagtgg t         41

<210> SEQ ID NO 148
<211> LENGTH: 41
<212> TYPE: DNA
<213> ORGANISM: Artificial Sequence
<220> FEATURE:
<223> OTHER INFORMATION: 3' CL primer, sense

<400> SEQUENCE: 148
gtcagcccac gaccaacctg ccggtcactc tgttcccgcc c         41

<210> SEQ ID NO 149
<211> LENGTH: 41
<212> TYPE: DNA
<213> ORGANISM: Artificial Sequence
<220> FEATURE:
<223> OTHER INFORMATION: 3' CL primer, sense

<400> SEQUENCE: 149
gtcagcccac gactgccctg ccggtcactc tgttcccrcc c         41

<210> SEQ ID NO 150
<211> LENGTH: 41
<212> TYPE: DNA
<213> ORGANISM: Artificial Sequence
<220> FEATURE:
<223> OTHER INFORMATION: 3' CL primer 1CL-BcgI-3', anti-sense
```

```
<400> SEQUENCE: 150
cagtcgggtg ctggttggac ggccagtgag acaagggcgg g                    41

<210> SEQ ID NO 151
<211> LENGTH: 41
<212> TYPE: DNA
<213> ORGANISM: Artificial Sequence
<220> FEATURE:
<223> OTHER INFORMATION: 3' CL primer 2CL-BcgI-3', anti-sense

<400> SEQUENCE: 151
cagtcgggtg ctgacgggac ggccagtgag acaagggygg g                    41

<210> SEQ ID NO 152
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated a

<400> SEQUENCE: 152
ncccgtacgc gcggcgaacg acg                                        23

<210> SEQ ID NO 153
<211> LENGTH: 24
<212> TYPE: DNA
<213> ORGANISM: Artificial Sequence
<220> FEATURE:
<223> OTHER INFORMATION: 5' end adaptor primer complement

<400> SEQUENCE: 153
gagcgtcgtt cgccgcgcgt acgg                                       24

<210> SEQ ID NO 154
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated c

<400> SEQUENCE: 154
ntccgtacgc gcggcgaacg acg                                        23

<210> SEQ ID NO 155
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated t

<400> SEQUENCE: 155
ncccgtacgc gcggcgaacg acg                                        23
```

<210> SEQ ID NO 156
<211> LENGTH: 23
<212> TYPE: DNA
<213> ORGANISM: Artificial Sequence
<220> FEATURE:
<223> OTHER INFORMATION: 5' end adaptor primer
<220> FEATURE:
<221> NAME/KEY: modified_base
<222> LOCATION: (1)...(1)
<223> OTHER INFORMATION: n = phosphorylated a

<400> SEQUENCE: 156
naccgtacgc gcggcgaacg acg                                            23

<210> SEQ ID NO 157
<211> LENGTH: 26
<212> TYPE: DNA
<213> ORGANISM: Artificial Sequence
<220> FEATURE:
<223> OTHER INFORMATION: 3' end adaptor primer complement

<400> SEQUENCE: 157
atgcttcaat accagctggg aggcct                                         26

<210> SEQ ID NO 158
<211> LENGTH: 23
<212> TYPE: DNA
<213> ORGANISM: Artificial Sequence
<220> FEATURE:
<223> OTHER INFORMATION: 3' end adaptor primer
<220> FEATURE:
<221> NAME/KEY: modified_base
<222> LOCATION: (1)...(1)
<223> OTHER INFORMATION: n = phosphorylated a

<400> SEQUENCE: 158
ngaggcctcc cagctggtat tga                                            23

<210> SEQ ID NO 159
<211> LENGTH: 23
<212> TYPE: DNA
<213> ORGANISM: Artificial Sequence
<220> FEATURE:
<223> OTHER INFORMATION: 3' end adaptor primer
<220> FEATURE:
<221> NAME/KEY: modified_base
<222> LOCATION: (1)...(1)
<223> OTHER INFORMATION: n = phosphorylated a

<400> SEQUENCE: 159
ntaggcctcc cagctggtat tga                                            23

<210> SEQ ID NO 160
<211> LENGTH: 27
<212> TYPE: DNA
<213> ORGANISM: Artificial Sequence
<220> FEATURE:
<223> OTHER INFORMATION: Vlambda structure after removal of unligated 5'
     adaptors
<220> FEATURE:
<221> NAME/KEY: misc_feature
<222> LOCATION: (23)...(27)
<223> OTHER INFORMATION: n = g, a, c or t

<400> SEQUENCE: 160
gcagcaagcg gcgcgcatgc ccannnn                                        27

```
<210> SEQ ID NO 161
<211> LENGTH: 32
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(3)
<223> OTHER INFORMATION: n = g, a, c or t

<400> SEQUENCE: 161
nnnctatccg gagggtcgac cataacttcg ta                                      32

<210> SEQ ID NO 162
<211> LENGTH: 30
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 162
nnnntgggca tgcgcgccgc ttgctgcgag                                         30

<210> SEQ ID NO 163
<211> LENGTH: 27
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (25)...(27)
<223> OTHER INFORMATION: n = g, a, c or t

<400> SEQUENCE: 163
agttatggtc gaccctccgg atagnnn                                            27

<210> SEQ ID NO 164
<211> LENGTH: 27
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (23)...(27)
<223> OTHER INFORMATION: n = g, a, c or t

<400> SEQUENCE: 164
gcagcaagcg gcgcgcatgc ctcnnnn                                            27

<210> SEQ ID NO 165
<211> LENGTH: 30
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(4)
<223> OTHER INFORMATION: n = g, a, c or t
```

<400> SEQUENCE: 165
nnnngaggca tgcgcgccgc ttgctgcgag                                              30

<210> SEQ ID NO 166
<211> LENGTH: 27
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (23)...(27)
<223> OTHER INFORMATION: n = g, a, c or t

<400> SEQUENCE: 166
gcagcaagcg gcgcgcatgc cctnnnn                                                 27

<210> SEQ ID NO 167
<211> LENGTH: 30
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 167
nnnnagggca tgcgcgccgc ttgctgcgag                                              30

<210> SEQ ID NO 168
<211> LENGTH: 27
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (23)...(27)
<223> OTHER INFORMATION: n = g, a, c or t

<400> SEQUENCE: 168
gcagcaagcg gcgcgcatgc caannnn                                                 27

<210> SEQ ID NO 169
<211> LENGTH: 30
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(4)
<223> OTHER INFORMATION: n = g, a, c or t

<400> SEQUENCE: 169
nnnnttggca tgcgcgccgc ttgctgcgag                                              30

<210> SEQ ID NO 170
<211> LENGTH: 32
<212> TYPE: DNA
<213> ORGANISM: Artificial Sequence

```
<220> FEATURE:
<223> OTHER INFORMATION: Vlambda structure after removal of unligated 5'
      adaptors
<220> FEATURE:
<221> NAME/KEY: misc_feature
<222> LOCATION: (1)...(3)
<223> OTHER INFORMATION: n = g, a, c or t

<400> SEQUENCE: 170
nnnctctccg gagggtcgac cataacttcg ta                                    32

<210> SEQ ID NO 171
<211> LENGTH: 27
<212> TYPE: DNA
<213> ORGANISM: Artificial Sequence
<220> FEATURE:
<223> OTHER INFORMATION: Vlambda structure after removal of unligated 5'
      adaptors
<220> FEATURE:
<221> NAME/KEY: misc_feature
<222> LOCATION: (25)...(27)
<223> OTHER INFORMATION: n = g, a, c or t

<400> SEQUENCE: 171
agttatggtc gaccctccgg agagnnn                                          27

<210> SEQ ID NO 172
<211> LENGTH: 16
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 172
cgcgcatgcc cannnn                                                      16

<210> SEQ ID NO 173
<211> LENGTH: 15
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (1)...(3)
<223> OTHER INFORMATION: n = g, a, c or t

<400> SEQUENCE: 173
nnnctatccg gaggg                                                       15

<210> SEQ ID NO 174
<211> LENGTH: 12
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 174
nnnntgggca tg                                                          12
```

<210> SEQ ID NO 175
<211> LENGTH: 19
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (16)...(19)
<223> OTHER INFORMATION: n = g, a, c or t

<400> SEQUENCE: 175
tcgaccctcc ggatagnnn                                                19

<210> SEQ ID NO 176
<211> LENGTH: 16
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 176
cgcgcatgcc tcnnnn                                                   16

<210> SEQ ID NO 177
<211> LENGTH: 12
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 177
nnnngaggca tg                                                       12

<210> SEQ ID NO 178
<211> LENGTH: 16
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 178
cgcgcatgcc ctnnnn                                                   16

<210> SEQ ID NO 179
<211> LENGTH: 12
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (1)...(4)
<223> OTHER INFORMATION: n = g, a, c or t

<400> SEQUENCE: 179
nnnnagggca tg                                                       12

```
<210> SEQ ID NO 180
<211> LENGTH: 16
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (13)...(16)
<223> OTHER INFORMATION: n = g, a, c or t

<400> SEQUENCE: 180
cgcgcatgcc aannnn                                              16

<210> SEQ ID NO 181
<211> LENGTH: 12
<212> TYPE: DNA
<213> ORGANISM: Artificial Sequence
<220> FEATURE:
<223> OTHER INFORMATION: amplified V-L cleaved by BssHII and SalI
<220> FEATURE:
<221> NAME/KEY: misc_feature
<222> LOCATION: (1)...(4)
<223> OTHER INFORMATION: n = g, a, c or t

<400> SEQUENCE: 181
nnnnttggca tg                                                  12

<210> SEQ ID NO 182
<211> LENGTH: 15
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (1)...(3)
<223> OTHER INFORMATION: n = g, a, c or t

<400> SEQUENCE: 182
nnnctctccg gaggg                                               15

<210> SEQ ID NO 183
<211> LENGTH: 19
<212> TYPE: DNA
<213> ORGANISM: Artificial Sequence
<220> FEATURE:
<223> OTHER INFORMATION: amplified V-L cleaved with BssHII and SalI
<220> FEATURE:
<221> NAME/KEY: misc_feature
<222> LOCATION: (16)...(19)
<223> OTHER INFORMATION: n = g, a, c or t

<400> SEQUENCE: 183
tcgaccctcc ggagagnnn                                           19
```